(12) United States Patent
Altman

(10) Patent No.: US 7,029,466 B2
(45) Date of Patent: Apr. 18, 2006

(54) CARDIAC DRUG DELIVERY SYSTEM AND METHOD FOR USE

(75) Inventor: Peter A. Altman, San Francisco, CA (US)

(73) Assignee: BioCardia, Inc., South San Francisco, CA (US)

( * ) Notice: Subject to any disclaimer, the term of this patent is extended or adjusted under 35 U.S.C. 154(b) by 210 days.

(21) Appl. No.: 10/265,429

(22) Filed: Oct. 3, 2002

(65) Prior Publication Data

US 2003/0032998 A1    Feb. 13, 2003

Related U.S. Application Data

(63) Continuation of application No. 09/057,060, filed on Apr. 8, 1998, now abandoned.

(51) Int. Cl.
*A61M 31/00* (2006.01)
*A61N 1/30* (2006.01)
*A61N 1/00* (2006.01)

(52) U.S. Cl. ............... 604/508; 604/21; 607/120; 607/122

(58) Field of Classification Search ............... 604/539, 604/264, 500, 523, 507, 508, 513, 511; 606/32, 606/41; 607/115, 119, 120–123; 600/374, 600/375
See application file for complete search history.

(56) References Cited

U.S. PATENT DOCUMENTS

| | | | | |
|---|---|---|---|---|
| 4,991,603 A | * | 2/1991 | Cohen et al. | 607/125 |
| 5,269,326 A | * | 12/1993 | Verrier | 600/374 |
| 5,829,447 A | * | 11/1998 | Stevens et al. | 128/898 |
| 5,860,951 A | * | 1/1999 | Eggers et al. | 604/510 |

* cited by examiner

*Primary Examiner*—Michael J. Hayes
(74) *Attorney, Agent, or Firm*—K. David Crockett, Esq.; Crockett & Crockett

(57) ABSTRACT

Implantable cardiac drug delivery systems. The systems are installed endocardially into a chamber in the heart, and are variously capable of delivering anti-arrhythmia agents into the heart wall, and into the epicardial space outside the heart, and into other chambers in the heart through the septa of the heart.

4 Claims, 19 Drawing Sheets

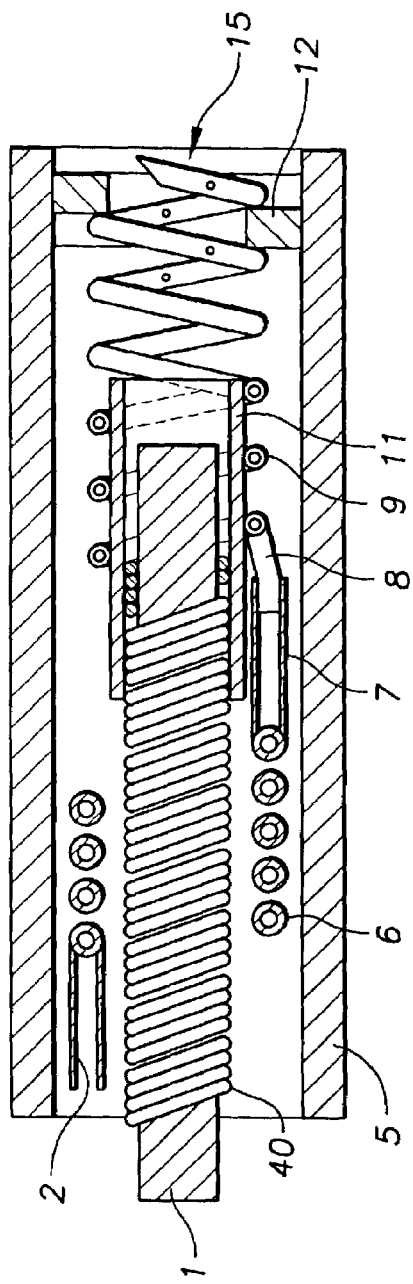
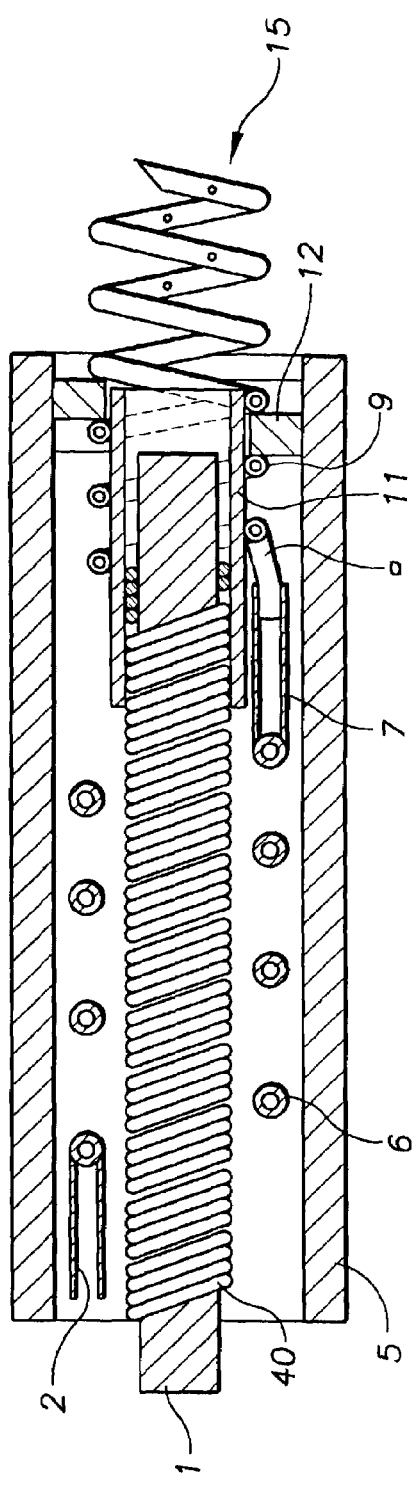
FIG.1Ea
FIG.1Eb

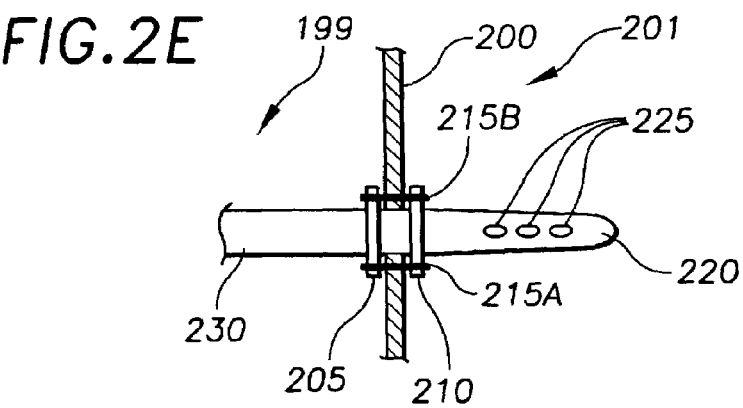
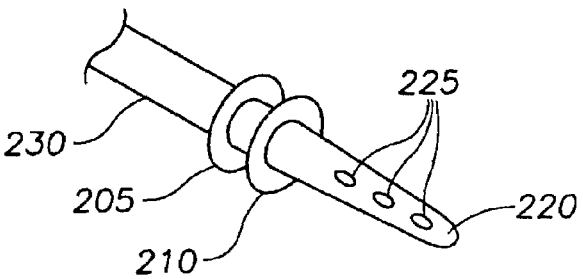
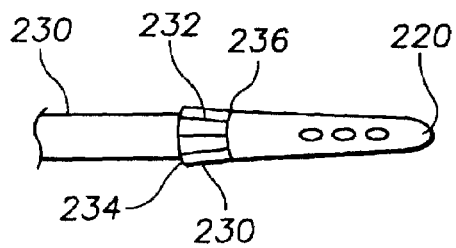
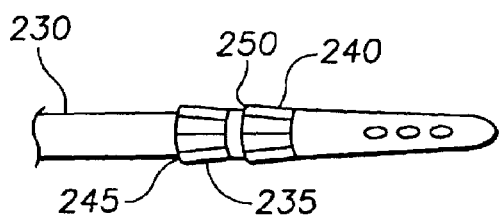
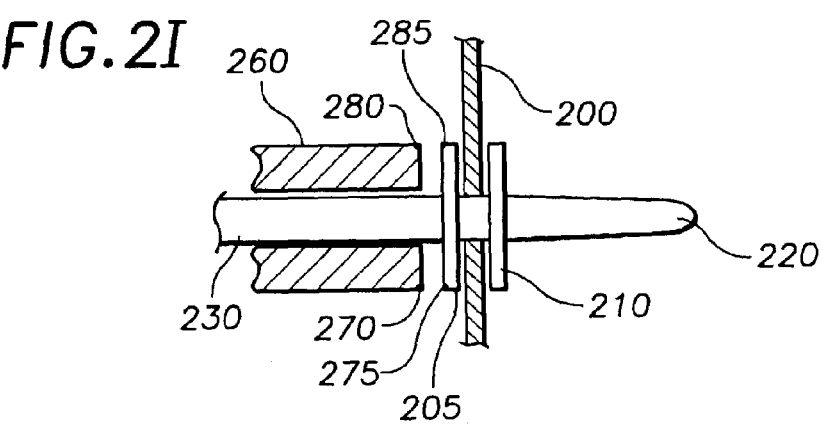

CARDIAC DRUG DELIVERY SYSTEM AND METHOD FOR USE

This application is a continuation of our co-pending application U.S. patent application Ser. No. 09/057,060 filed Apr. 8, 1998, the specification of which is incorporated by reference.

FIELD OF THE INVENTION

The inventions described below relate to the field of cardiovascular drug delivery, including systems and methods for providing local transient pharmacological therapy to the myocardium.

BACKGROUND OF THE INVENTION

Atrial fibrillation is a form of heart disease that afflicts millions of people. It is a condition in which the normal contraction of the heart is interrupted, primarily by abnormal and uncontrolled action of the atria of the heart. The heart has four chambers: the right atrium, right ventricle, the left ventricle, and the left atrium. The right atrium pumps de-oxygenated blood from the vena cava to the right ventricle, which pumps the blood to the lungs, necessary for return flow of de-oxygenated blood from the body. The right atrium contracts to squeeze blood into the right ventricle, and expands to suck blood from the vena cava. The contractions normally occur in a controlled sequence with the contractions of the other chambers of the heart. When the right atrium fails to contract, contracts out of sequence, or contracts ineffectively, blood flow within the heart is disrupted. The disruption of the normal rhythm of contraction is referred to as an arrhythmia. The arrhythmia known as atrial fibrillation can cause weakness due to reduced ventricular filling and reduced cardiac output, stroke due to clot formation in a poorly contracting atria (which may lead to brain damage and death), and even other life threatening ventricular arrhythmias.

Atrial defibrillator is a therapy being developed for atrial fibrillation. Atrial defibrillators are typically implantable electrical therapy devices which deliver defibrillating energy to the atrium to terminate arrhythmias. They sense the electrical activity of the atrium and deliver an electrical shock to the atrium when the electrical activity indicates that the atrium is in fibrillation. Electrical defibrillation has two major problems: the therapy causes substantial pain and has the potential to initiate a life threatening ventricular arrhythmia. The pain associated with the electrical shock is severe and unacceptable for many patients. Unlike electrical ventricular defibrillators where the patient loses consciousness prior to receiving therapy, the patient who suffers an atrial arrhythmia is conscious and alert when the device delivers electrical therapy.

The potential exists for inappropriate induction of ventricular fibrillation by the shock intended to defibrillate the atrium. The induction of ventricular fibrillation has great potential to result in death in just a few minutes if no intervening therapy is provided. Careful algorithms to deliver shocks to the periods in the ventricular contraction cycle when the heart is not susceptible to shock induced ventricular fibrillation have been developed to reduce the potential of this risk. If the problem of patient pain can be overcome, atrial defibrillators could be used in a large portion of the patient population that suffer from atrial fibrillation.

Pharmacological Atrial Defibrillators

For some time, doctors have treated atrial fibrillation with drugs injected intravenously or administered orally. Recent literature describes the potential for the delivery of drugs to the heart on demand to terminate arrhythmias. The concept has been suggested for use in the atrium to treat atrial fibrillation. Arzbaecher, Pharmacologic Atrial Defibrillator and Method, U.S. Pat. No. 5,527,344 (Jun. 18, 1996) describes a pharmacological atrial defibrillator and method for automatically delivering a defibrillating drug into the bloodstream of a patient upon detection of atrial arrhythmias in order to terminate the atrial arrhythmias. Arzbaecher teaches that unspecified defibrillating drugs should be injected into the bloodstream with a large initial dose followed by delivery of a continuous smaller dose (this is the "two-compartment pharmacokinetic model" discussed in the Arzbaecher patent). By delivering agents to a blood vessel and maintaining a therapeutic level of drugs in the blood stream, Arzbaecher requires systemic effects to be achieved in order to terminate atrial arrhythmias. In other words, if drugs injected according to Arzbaecher are to have any effective concentrations within the heart, a large amount must be injected in the blood stream to ensure that an adequate dose will be delivered to the affected area of the heart. While the drugs are in the blood stream, they are available throughout the body to cause side effects on all other organs.

There are several disadvantages to the transient introduction of systemic drug levels by an implantable device. Systemic effects resulting from such delivery may result in detrimental effects to ventricular cardiac conduction. These detrimental effects could be life threatening. The large amount of drugs required for systemic delivery of therapeutic doses demands a larger, less comfortable device than smaller dosages would allow. The large quantity of drug in the implantable reservoir of such a system is potentially more dangerous if it develops a leak or is ruptured. Such a large single dosage will require a reservoir that requires frequent follow ups for refilling post therapy by a clinician. Lastly, the large quantities of drug required to obtain therapeutic levels in the entire body may cost substantially more than that required to treat a specific site within the heart. The system described by Arzbaecher has one primary advantage over electrical atrial defibrillation: the delivery of therapy to terminate an arrhythmia does not cause patient pain, and some recent abstracts have appeared in the literature which suggest that this technique is viable. See Arzbaecher, et al., Development Of An Automatic Implanted Drug Infusion System For The Management Of Cardiac Arrhythmias, 76 IEEE Proc. 1204 (1991); Bloem, et al., Use Of Microprocessor Based Pacemaker To Control An Implantable Drug Delivery System, Computers in Cardiology 1 (1993); Bloem, et al., Microprocessor Based Automatic Drug Infusion System For Treatment Of Paroxysmal Atrial Fibrillation, 26S J. Electrocardiogr. 60 (1993); and Wood, et al., Feedback control of antiarrhythmic agents, in *Molecular Interventions and Local Drug Delivery*, (W B Saunders 1995).

Drug delivery directly into the heart has been proposed for other conditions. In my own prior patent, Altman, Implantable Device for the Effective Elimination of Cardiac Arrythmogenic Sites, U.S. Pat. No. 5,551,427 (Sep. 3, 1996) I describe an implantable substrate for local drug delivery at a depth within the heart. The patent shows an implantable helically coiled injection needle which can be screwed into the heart wall in the ventricles and connected to an implanted drug reservoir outside the heart. This system allows injection of drugs directly into the wall of the heart by merely the injection of drugs through the skin into the reservoir. The patent also shows a helical coil coated with a coating which releases drug into the myocardium. This drug delivery may be performed by a number of techniques, among them infusion through a fluid pathway, and delivery from controlled release matrices at a depth within the heart. Co-pending application Ser. No. 08/881,685 by Altman and Altman, describes some additional techniques for delivering local pharmacological agents to the heart.

Other implanted drug delivery systems have been proposed. Levy, System for Controlled Release of Antiarrhythmic Agents, U.S. Pat. No. 5,387,419 (Feb. 7, 1995), describes the placement of controlled release matrices on the surface of the epicardium (on the outside of the heart) for delivery of antiarrhythmic agents, but all dosage forms described are for steady state drug delivery and do not address the advantages of transient drug delivery from an implantable epicardial structure. In addition, the device described by Levy does not address the critical issue of surgical access to the epicardial surface.

Controlled release matrices are drug polymer composites in which a pharmacological agent is dispersed throughout a pharmacologically inert polymer substrate. Sustained drug release takes place via particle dissolution and slowed diffusion through the pores of the base polymer. Prior work has shown that antiarrhythmic therapy administered by epicardial application of controlled release polymer matrices is effective in treating and preventing ventricular arrhythmias in canine ventricular tachycardia model systems [Siden, et al., Epicardial Controlled Release Verapimil Prevents Ventricular Tachycardia Episodes Induced by Acute Ischemia in a Canine Model, 19 J. Cardiovascular Pharmacology 798 (1992).] This work shows the viability of controlled release therapy delivered locally for the treatment of arrhythmias. This work is identical to that described by Levy above in that drug delivery structures are placed on the outside surface of the heart during open heart surgery. No delivery at a depth within the heart is described, there is no discussion of how one would implant the structure non-invasively, and there is no discussion of how one would deliver drugs upon demand to the heart.

Cardiac Pacing

In the past, devices implanted into the heart have been treated with anti-inflammatory drugs to limit the inflammation of the heart caused by the wound incurred while implanting the device itself. For example, pacing leads have incorporated steroid drug delivery to limit tissue response to the implanted lead, and to maintain the viability of the cells in the region immediately surrounding the implanted device. Berthelson, Medical Electrical Lead Employing Improved Penetrating Electrode, U.S. Pat. 5,002,067 (Mar. 26, 1991) describes a helical fixation device for a cardiac pacing lead with a groove to provide a path to introduce anti-inflammatory drug to a depth within the tissue. The groove does not provide a patent fluid pathway to a depth within the heart, no tube end to end is described, and the device is designed for pacing the heart. No descriptions of using antiarrhythmic agents or other approaches are described.

Moaddeb, Myocardial Steroid Releasing Lead, U.S. Pat. No. 5,324,325 (Jan. 24, 1994) describes a myocardial steroid releasing lead whose tip of the rigid helix has an axial bore which is filled with a therapeutic medication such as a steroid or steroid based drug. There is no fluid pathway from the proximal end of the catheter, the drug delivery structure is limited in its size, the device is designed for cardiac pacing. Moaddeb describes a reservoir that is small in that it fills only the core region of the distal portion of a helix historically formed of 0.010 inch diameter to 0.012" diameter wire.

Vachon, Implantable Stimulation Lead Having an Advanceable Therapeutic Drug Delivery System, U.S. Pat. No. 5,447,533 (Sep. 5, 1995) and U.S. Pat. No. 5,531,780 (Jul. 2, 1996) describe pacing leads having a stylet introduced anti-inflammatory drug delivery dart and needle which is advanceable from the distal tip of the electrode. No end to end tube is provided, and no means for transient delivery of agents in an implantable setting is provided.

Cardiac Ablation

The infusion of different fluids to a depth within the myocardium has been described in the patent literature as being useful for ablation. Lesh, Cardiac imaging and ablation catheter, U.S. Pat. No. 5,385,148 (Jan. 31, 1995) describes a cardiac imaging and ablation catheter in which a helical needle may be used to deliver fluid ablative agents, such as ethanol, at a depth within the tissue to achieve ablation. Lesh proposes permanently killing the tissue with a one time application of ethanol such that the heart is permanently damaged, not controlled. In one embodiment he does describe the potential of temporarily deadening the tissue with either lidocaine or iced saline solution, but this is merely in preparation of killing the tissue. The entire patent here teaches away from implantable materials and applications as the fundamental device use is for acute ablation procedures. No means for transient delivery of agents in an implantable setting is provided.

Mulier, Method and Apparatus for Ablation, U.S. Pat. No. 5,405,376 (Apr. 11, 1995), Method and Apparatus for R-F Ablation, U.S. Pat. No. 5,431,649 (Jul. 11, 1995); and Method for R-F Ablation, U.S. Pat. No. 5,609,151 (Mar. 11, 1997) each describe a hollow helical delivery needle to infuse the heart tissue with a conductive fluid prior to ablation to control the lesion size produced. In addition delivery of an agent to affect cardiac conduction to evaluate an ablation site, and delivery of RF energy to the helical needle are disclosed. In all embodiments the device is described as an acute use ablation catheter using different techniques. No means for transient delivery of agents in an implantable setting is provided.

Cardiovascular Restenosis

Igo, Apparatus And Method For Transpericardial Delivery of Fluid, U.S. Pat. No. 5,634,895 (Jun. 3, 1997) shows a technique for delivering drugs locally to different regions of the surface of the heart and within the pericardial sac via a subxiphoid surgical route, for treating vascular thrombosis and restenosis. The subxiphoid surgical route requires open chest surgery, and penetration of the pericardial sac. Such invasive procedures can be complicated by pericarditis and pericardial tamponade. No techniques for less invasive delivery of bioactive agents to the surface of the heart or into the pericardial space are described. No systems for transient delivery, or transient delivery upon demand are described. No techniques for delivering antiarrhythmic agents or terminating atrial arrhythmias are addressed.

Antiarrhythmic Drugs

There are a number of viable pharmacologic therapies that are also available. Drugs that predominantly affect slow pathway conduction include digitalis, calcium channel blockers, and beta blockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propafenone). The class III antiarrhythmic agents (sotolol or amiodorone) prolong refractoriness and delay or block conduction over fast or slow pathways as well as in accessory AV connections. Temporary blockade of slow pathway conduction usually can be achieved by intravenous administration of adenosine or verapamil. [Scheinman, Supraventricular Tachycardia: Drug Therapy Versus Catheter Ablation, 17 Clinical Cardiology II-11 (1994)]. Other agents such as encainide, diltiazem, and nickel chloride are also available.

Drugs currently used for antiarrhythmia control can actually kill people. The Cardiac Arrhythmia Suppression Trial showed that specific agents delivered systemically resulted in substantially higher mortality rates than those individuals receiving no drugs at all. [The Cardiac Arrhythmia Suppression Trial (CAST) Investigators, The effect of encainide and flecainide on mortality in a randomized trial of arrhythmia suppression after myocardial infarction, 321 N. Engl. J. Med. 406 (1989). Echt, et al., Mortality and morbidity in patients receiving encainide, flecainide, or placebo—the Cardiac Arrhythmia Suppression Trial, 324 N. Engl. J. Med. 781 (1991).] This is likely due to the problematic pro-arrhythmia effects of systemic drug delivery. Minimization of dose by local transient drug delivery has potential to eliminate the side effects of these antiarrhythmic agents. There is a need to improve pharmacological therapy for the treatment of arrhythmias by providing for local delivery of these and other agents to regions within the heart tissue.

There are embodiments of this invention which incorporate noninvasive surgical techniques for delivering drugs to the pericardial space and overcoming the difficulties of the invasive sub-xiphoid procedure described by Igo. In order to develop these techniques it is important to touch on the prior art regarding pericardial access and delivery.

Pericardial Access and Delivery

There are a number of approaches for placing devices epicardially. Crosby, Apparatus for cardiac surgery and treatment of cardiovascular disease, U.S. Pat. No. 4,181,123 (Jan. 1, 1980) and Method And Apparatus For Permanent Epicardial Pacing Or Drainage Of Pericardial Fluid And Pericardial Biopsy, U.S. Pat. No. 4,319,562 (Mar. 16, 1982) and Chin, et al., Method And Apparatus For Providing Intrapericardial Access And Inserting Intrapericardial Electrodes, U.S. Pat. No. 5,033,477 (Jul. 23, 1991) to disclose methods for placing electrodes in contact with the heart muscles from within the pericardial space without the need for a thoracotomy. Access to the pericardial space is gained via a sub xiphoid approach. This involves penetrating the chest wall below the xiphoid process.

The sub xiphoid route has several disadvantages. First, because the pericardial sac which surrounds the heart is a tight fitting fibrous membrane, the pericardial space is so small that it is difficult to penetrate the sac without also puncturing, and thereby damaging the heart itself. Second, accessing the heart via a subxiphoid route entails a high risk of infection. These are likely to account for the failure of these methods to be adopted in common clinical practice.

Several patents, including Elliott, et al., Method For Transvenous Implantation Of Objects Into The Pericardial Space Of Patients, U.S. Pat. No. 4,884,567 (Dec. 5, 1989) and Elliott, Defibrillator System With Cardiac Leads And Method For Transvenous Implantation, U.S. Pat. No. 4,946,457 (Aug. 7, 1990) and Cohen, et al., Travenously Placed Defibrillation Leads, U.S. Pat. No. 4,998,975 (Mar. 12, 1991) have proposed methods for transvenous implantation of electrodes into the pericardial space. A catheter is introduced through a vein to the right atrium where the lateral wall is penetrated in order to introduce electrodes into the pericardial space. A major problem encountered by these methods is how to penetrate the lateral atrial wall without puncturing the tight fitting pericardium.

The methods of these patents attempt to solve this problem through several elaborate schemes. One scheme involves using complex catheters to attach to the lateral wall and to pull it back away from the pericardium prior to penetrating the atrial wall in order to avoid puncturing the pericardium. Another approach involves injecting a fluid into the pericardial space to distend the pericardium away from the lateral atrial wall prior to penetrating the wall.

Cohen, Method and System for Implanting Self Anchoring Epicardial Defibrillation Electrodes, U.S. Pat. No. 4,991,578 (Feb. 12, 1991) discloses a method for implanting epicardial defibrillation electrodes into the pericardial space via the subxiphoid route. As discussed above, it is difficult to penetrate the pericardial sac via the sub xiphoid route without also puncturing and thereby damaging the heart itself. Like the method discussed directly above, the '578 patent discloses injecting a fluid into the pericardial space or attaching and pulling on a catheter to distend the pericardial sac away from the heart.

Cohen, Transvenously Placed Defibrillation Leads Via An Inferior Vena Cava Access Site And Method Of Use, U.S. Pat. No. 4,991,603 (Feb. 12, 1991) discloses a method for implanting defibrillation electrodes in contact with epicardial or pericardial tissue from an inferior vena cava access site. A hole is made in the inferior vena cava and a catheter is transvenously inserted into the inferior vena cava and out through a hole into the chest cavity adjacent to the heart. The catheter then pierces the pericardial sac to access the pericardial space. The risk of damaging the heart muscle remains high with this method.

The pericardial sac has been used for containment of pharmacological agents for a number of years in experimental settings, but delivery has required open chest surgery to access the pericardial space. Ellinwood, Apparatus And Method For Implanted Self-Powered Medication Dispensing, U.S. Pat. No. 4,003,379 (Jan. 18, 1977) and Ellinwood, Self-Powered Implanted Programmable Medication System And Method, U.S. Pat. No. 4,146,029 (Mar. 27, 1979) disclose an implantable medication dispensing apparatus which is adapted to dispense drugs to the pericardial sac over a long period of time, for example to prevent arrhythmias. The Ellinwood patents do not teach a method for routing drugs to the pericardial sac. Epicardial delivery of pharmacological agents to the heart is similar to that described in Igo, Apparatus And Method For Transpericardial Delivery Of Fluid, U.S. Pat. No. 5,634,895 (Jun. 3, 1997) which describes a balloon catheter for sub xiphoid access. Levy, System for controlled release of antiarrhythmic agents, U.S. Pat. No. 5,387,419 (Feb. 7, 1995) describes implantable control release matrices. Verrier, Method For Transvenously Accessing The Pericardial Space Via The Right Auricle For Medical Procedures, U.S. Pat. No. 5,269,326 (Dec. 14, 1993) describes a technique for accessing the pericardium through the right atrial appendage and describes the possibility of infusing the pericardium with antiarrhythmic agents.

No systems or techniques for local drug delivery to the epicardial surface of the heart upon demand have been described. In addition, no means of creating a viable atriotomy closure after transatrial implantation of devices has been described. Further, no means has been provided for hybrid local drug delivery therapies involving electrical therapy and ablative therapy for the treatment of arrhythmias.

SUMMARY OF THE INVENTION

Several inventions described below permit local transient therapy for arrhythmias. Drugs or other anti-arrhythmia agents may be delivered into one or more regions of the atrial or ventricular wall to control arrhythmia of the atrium or ventricle with devices implanted into the chest, including a drug delivery catheter with a tip for implantation into the heart wall and a drug reservoir implanted in the chest. The devices can deliver drugs into the wall of the heart, into the left atrium through a catheter which is implanted in the right atrium, and into the left ventricle which is implanted in the right ventricle. The devices may be combined with other therapies such as implantable defibrillators and cardiac pacemakers. The devices may also be used to transiently created a long linear lesion within the atrium or used to augment the effects of a region of permanent ablation transiently. Different embodiments of the systems described may be used together.

BRIEF DESCRIPTION OF THE DRAWINGS

FIGS. 2b through 2d are detail views of the system of FIG. 2a.

FIGS. 2e through 2i illustrate catheters for transatrial access to the epicardial space.

FIGS. 2P through 2Qb are detail views of the system of FIG. 2k.

DESCRIPTION OF INVENTION

The description of this invention will be broken down into three parts which inter-relate to one another: (I) the method and devices for local delivery to the heart, (II) the methods and devices for transient delivery of agents to the local drug delivery systems described, and lastly (III) hybrid therapies of such delivery systems and transient delivery techniques combined with other therapies.

Part I: Method and Devices for Local Delivery to the Heart

Delivery from a Penetrating Structure

One embodiment for extremely local delivery of agents to the myocardium involves a penetrating structure that has a fluid pathway to a depth within the myocardium for local infusion of pharmacological agents on demand. Such implantable infusion devices are described by Altman in U.S. Pat. No. 5,551,427 as well as in a pending patent application U.S. patent application Ser. No. 08/881,685 filed by Altman and Altman. Both of these should be incorporated here by reference.

For example, a single point source of pharmacological agents delivered to a depth within the atrial tissue will enable a region of atrium to be pharmacologically modified while the systemic doses are extremely small. This will act as a region of slowed conduction on which the wave fronts associated with atrial fibrillation will be terminated. Unlike the transient effects of a paced site, a site infused with drug will have slowed conduction for a substantial period of time. The longer the drug is infused to the site, the larger the region of inactive atrium will be. Very small doses can be delivered to specific regions of tissue to terminate arrhythmias. Systemic effects will be minimized. The quantity of agents will be minimized, as will reservoir size and number of physician follow-ups.

Figure 1:
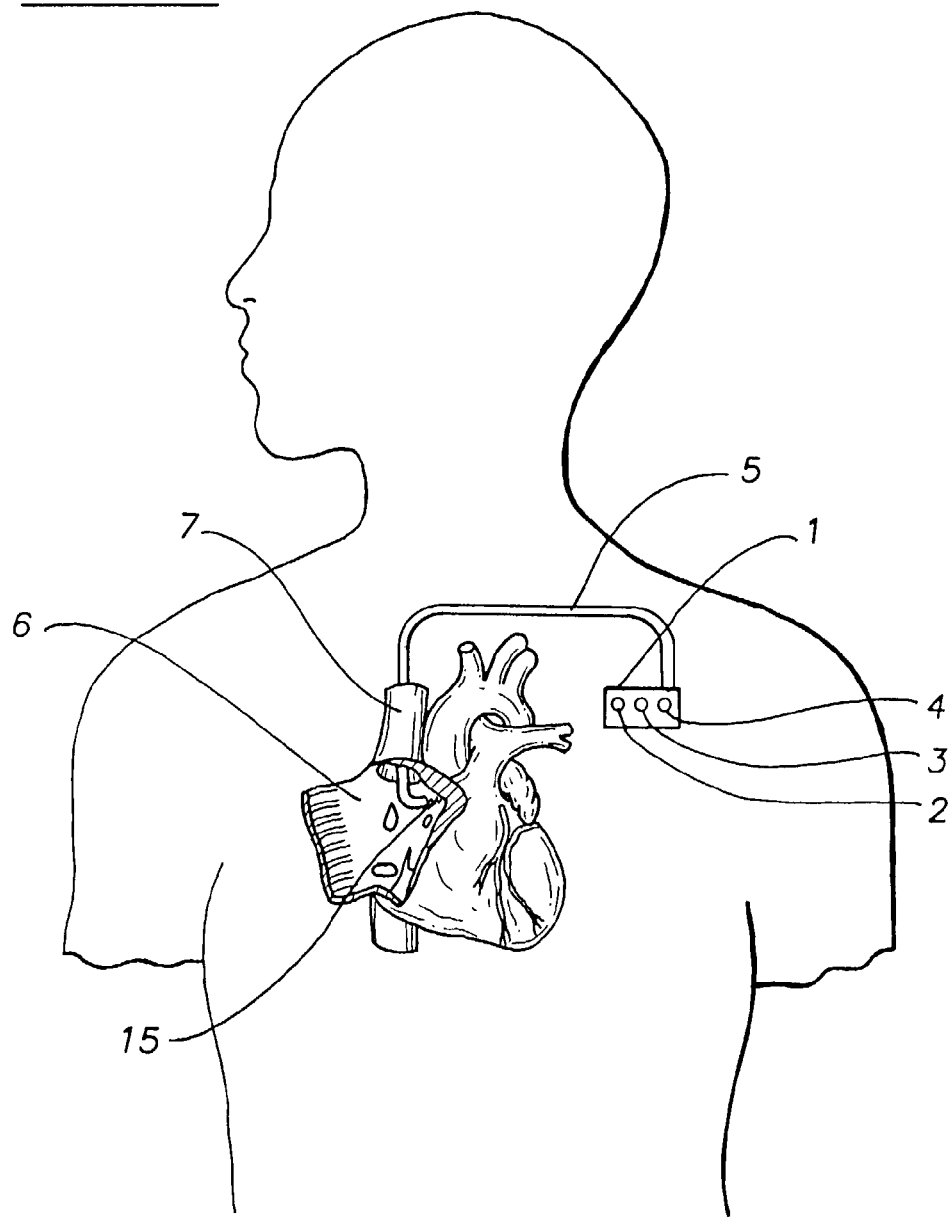
FIG. 1 is an overview of an implantable cardiac drug delivery system.

FIG. 1 shows a detailed drawing of a technique described substantially in Altman, U.S. Pat. No. 5,551,427, as well as in a pending patent application Ser. No. 08/881,685 filed by Altman and Altman. Shown here is a subcutaneously implanted fluid pump 1 having a plurality of silicone septii 2 and 3 on its upward facing surface to facilitate the filling of drug reservoirs within pump 1. Also shown on the surface of pump 1 is a pressure switch 4 which enables the patient to mechanically turn on the pumping mechanism when judged appropriate. Pump 1 is connected to catheter 5 which travels transvenously by way of the subclavian vein (not shown) through the superior vena cava 7 and into the right atrium 6 which is shown in a cut away view. These implantation techniques are well known to those familiar with the placement of implantable cardiac leads. The penetrating drug delivery structure, shown here as helix 15 on the end of catheter 5 is in fluid connection with pump 1 such that drugs can be delivered directly to a depth within the atrial wall tissue. The region within the atrium of implantation specified may vary from patient to patient based on the characteristics of the atrial arrhythmia being treated. Here it is shown placed in the intra atrial septum which has been, described as important for the termination of atrial fibrillation.

Figure 1A:
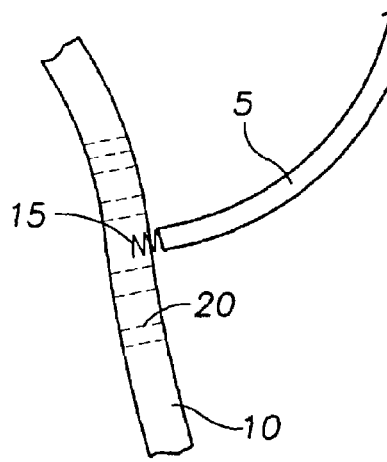
FIGS. 1a through 1d are detail views of the system of FIG. 1.

FIG. 1A shows the distal end of catheter 5 shown in FIG. 1. Catheter body 5 may enclose helical wire or cabled wire conductors for monitoring the electrical activity of the heart or delivering pacing energy which is coupled to hollow fixation structure 15 which delivers drugs to a depth within the heart tissue 10. The progression of the drug transport 20 from the site of the drug delivery helix 15 can be monitored during implantation in a number of ways. Either pacing thresholds can be measured which will be higher and correlate to a larger infused volume, or endocardial electrophysiology mapping can be performed if desired.

Figure 1B:
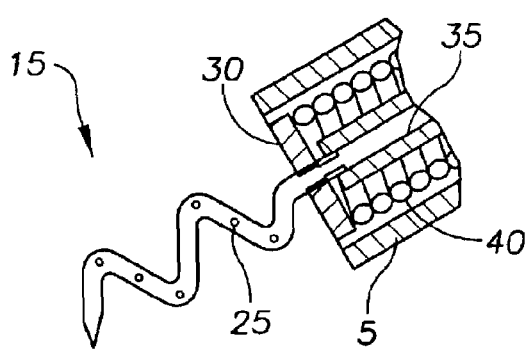

An enlarged view of this drug delivery lead is shown in FIG. 1B. Here, hollow fixation structure 15 is shown to have a number of apertures 25 along its length, and be connected on its proximal end to both a tube 35 for drug delivery and a helical coil 40 for the measurement of electrical signals from the heart and the delivery of pacing energy. Structure 30 is made of an electrically conductive material and stabilizes the hollow drug delivery structure and allow for its connection to the conductive coil 40.

Figure 1C:
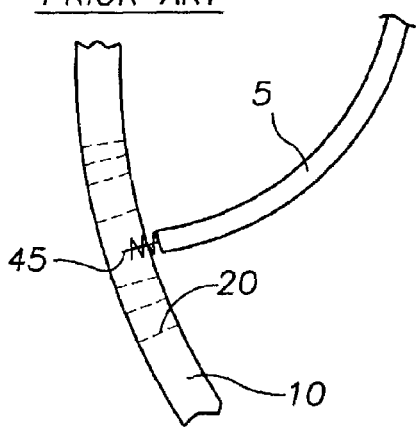
Figure 1D:
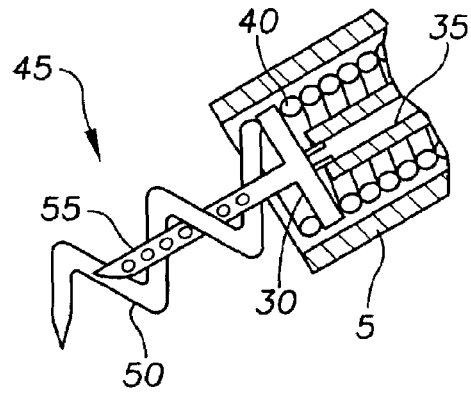

FIG. 1C shows another embodiment very similar to FIG. 1A except here, the penetrating structure 45 is composed of two elements. In the expanded view shown in FIG. 1D the two elements are a fixation helix 50 and a centrally located needle 55 which is porous over some region. It should be clear that it would be very easy to design needle 55 so that it is not centrally located. This hollow needle 55 is connected to the tube 35, and is also connected electrically to the coil 40 and the helix 50. It would be straightforward to make the needle or the helix the sole penetrating conductive element connected to the coil 40.

FIG. 1E*a* and FIG. 1E*b* show another embodiment in partial cross section that is similar to FIG. 1A. Here, a stylet wire 1 is inserted into coil 40 and is used for steering the catheter structure to a particular location as well as for deploying penetrating helix 15 for infusing therapeutic fluid agents. Adjacent to coil 40 is a drug delivery tube 2 which wraps helically around coil 40 and is advanced in a region 7 over the hollow tube or needle 8 which allows for fluid agents to be delivered either to a depth within the tissue, or through the tissue. Stylet 1 is able to transmit torque to distally located structure 11 by having the stylet's distal cross section have one axis longer than the other, such as an oval or rectangle and by having structure 11 be shaped similarly such that stylet 1 fits within distal structure 11. Here distal structure 11 is shown to be press fit onto the outside of coil 40 and to the inside of fixation helix 15 shown here to have a hollow cross section 9. Other means of joining these structures such as crimping, swaging, welding, brazing, and bonding are also possible. Further, the distal structure 11 may have different cross sectional shapes along its length to provide for attachment, torque transmission, and electrical continuity to fixation structure 15. Upon transmission of torque to distal structure 11, the helix 15 advances through structure 12 and out the distal end of the catheter to engage the tissue (not shown). The helical wrapping of drug delivery tube 2 distends as shown by the difference in FIGS. 1E*a* and 1E*b* such that the fluid connections to the penetrating structure and the proximal connections (not shown) are not stressed. A distensible fluid pathway such as that shown could be located at different regions along the catheter body, and not just at the distal end as shown here. By placing it at the distal end, a bi-lumen tubing could be used along the length of the catheter until the region where the distensible drug delivery tubing is located, and an appropriate transition (not shown) to a single lumen tubing such as is shown could be implemented.

Figure 1F:
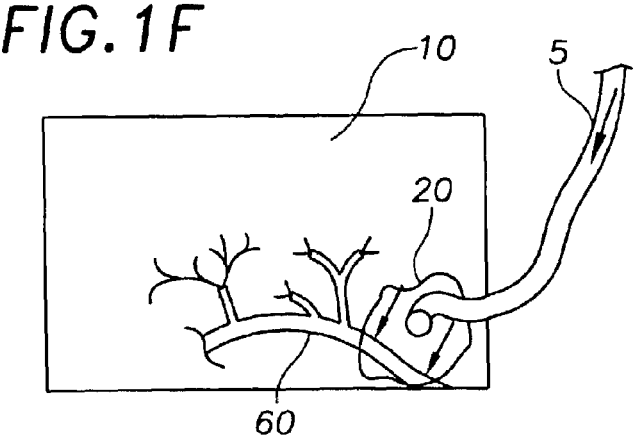
FIGS. 1Ea through 1F illustrate a new use of the system of FIG. 1.

FIG. 1F shows a view similar to that shown in 1C, except now the drug is delivered adjacent to a blood vessel 60 such that the drug can percolate across the vessel wall and enter into the blood pool that feeds this local tissue 10. For example, in the treatment of supraventricular arrhythmias, a catheter placed in the right atrium may be implanted in the free heart wall such that its drug delivery structure may deliver to vessels such as the right coronary artery (RCA), the sinus node branch of the RCA, the conus branch of the RCA, the atrioventricular node branch of the RCA, and the posterior descending interventricular branch of the RCA. The flow from the catheter forces retrograde flow up regions of the capillaries up the arterioles and into the larger coronary artery. The drugs delivered in the coronary artery are then distributed to portion of the myocardium that is supplied by the coronary artery.

Delivery from an Epicardial Structure

Figure 2A:
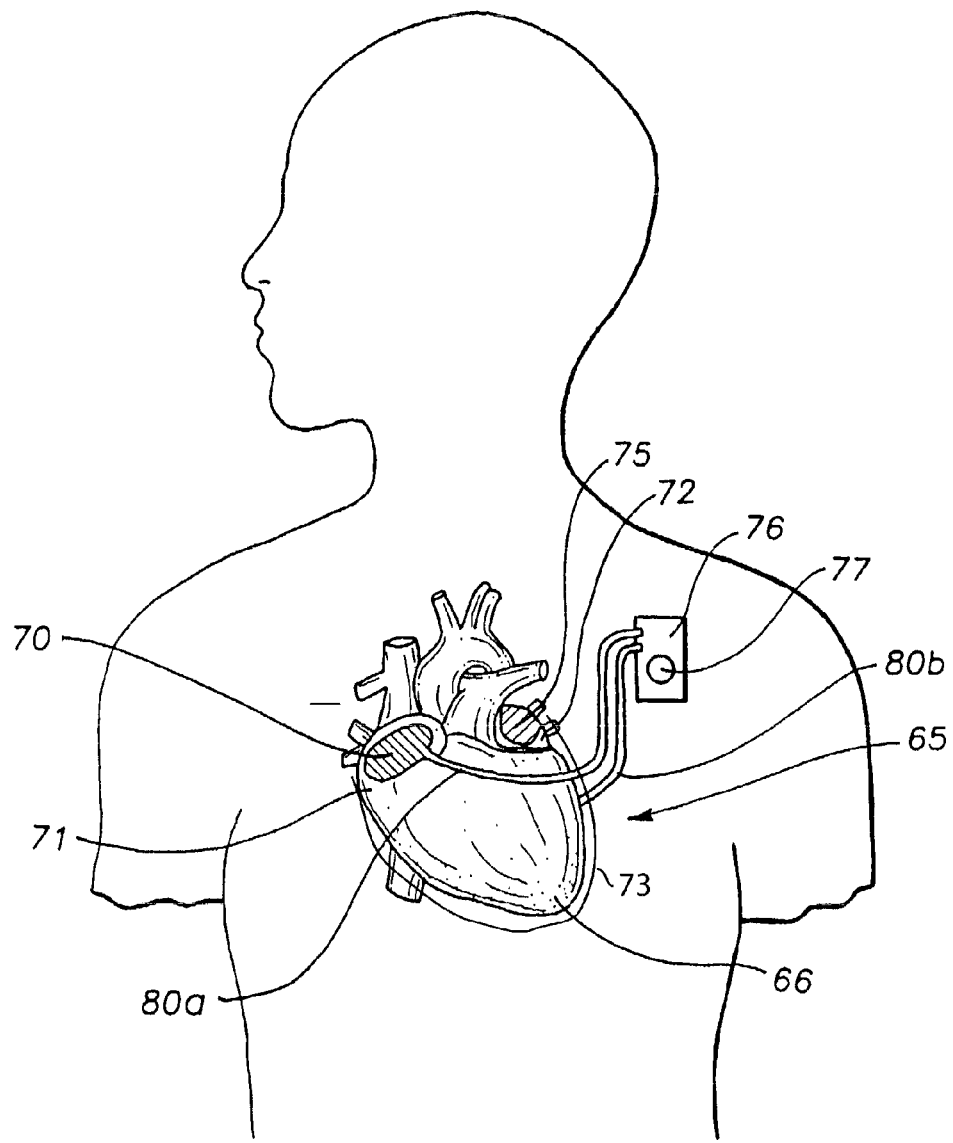
FIG. 2a is an overview of an implantable epicardial drug delivery system.

FIG. 2A shows an intact heart 65 with ventricles 66, and right atria 71 and left atria 72. Two epicardial drug delivery patches 70 and 75 disposed within the pericardial (or epicardial) space 73 surrounding the heart and covering the right atria 71 and left atria 72, respectively. These patches are shown to be connected to separate but identical thin drug delivery catheters 80*a* and 80*b* which connect the drug delivery patch structure to the implantable pump 76 which is located subcutaneously in the pectoral region. Drug delivery patches are placed over the atria 71 and 72 to minimize the drug delivery to the ventricles and to maximize the delivery to the atria, although it is clear that the opposite scenario is also possible. Drug delivery catheters 80*a* and 80*b* contain a fluid pathway from drug delivery patches 70 and 75 for the infusion of agents upon demand. Catheters 80*a* and 80*b* may also contain electrical conductors which connect to the drug delivery patches to either perform electrical measurements on the activation of the heart, stimulate the heart, or facilitate delivery from the drug delivery structure by opening some electromechanical valve in the distal region.

Figure 2B:
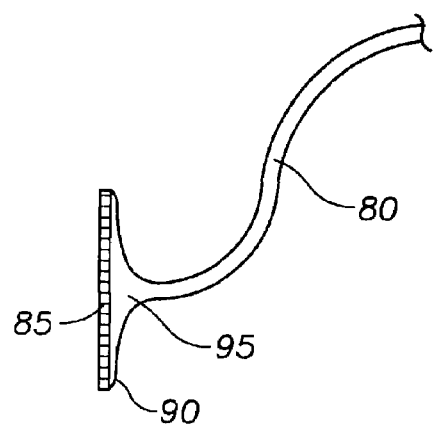

FIG. 2B shows a side view of these same patch drug delivery systems in which tube 80 allows the flow of fluid agents to the thin space 95 which serves as a plenum, communicating with a fluid resistant mesh 85. The fluid resistant mesh 85 serves as a diffusing medium which allows the small volume of drug in space 95 to be uniformly distributed over the surface area of the patch as it is delivered. In this way, a large surface of the heart is treated simultaneously. Mesh 85 could also be a rate limiting membrane. The rate limiting membrane could be made of ePTFE with small pores such that the drug distributes more readily over the surface of the rate limiting barrier inside the drug delivery patch than it does through the rate limiting barrier. This will prevent all of the fluidic agent from being delivered at the point where it enters the large surface of delivery patch. Such rate limiting membranes and materials are well known in the field of transdermal drug delivery systems, but have not been used in cardiac drug delivery systems. Alternatively, the barrier could be a thin hydrogel or other material through which the delivery would be required to diffuse more slowly. There is a rim 90 around the drug delivery surface defined by mesh 85 such that the patch may be sewn onto the surface of the heart, or to the inside of the pericardial sac such that the drug delivery surface is in contact within the epicardium.

Figure 2C:
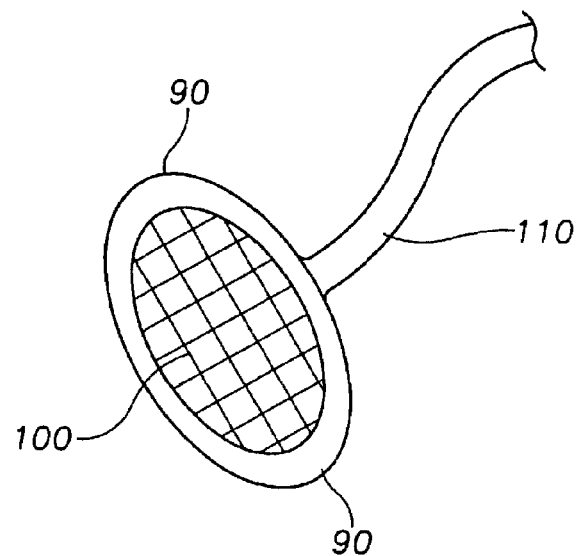

FIG. 2C shows yet another embodiment of this patch drug delivery system approach which includes an electrically conductive surface. Here electrically conductive Titanium or Platinum mesh 100 is in contact with the heart such that electrical signals on the surface of the heart or electrical energy can be delivered to the heart. The mesh is installed on the patch over the rate limiting membrane 85 (not shown). Catheter body 110 includes both a fluid pathway for drug delivery and the electrical conductor which connects to mesh 100. Rim 90 is provided to suture the patch to either the epicardium or the inside of the pericardial sac.

Figure 2D:
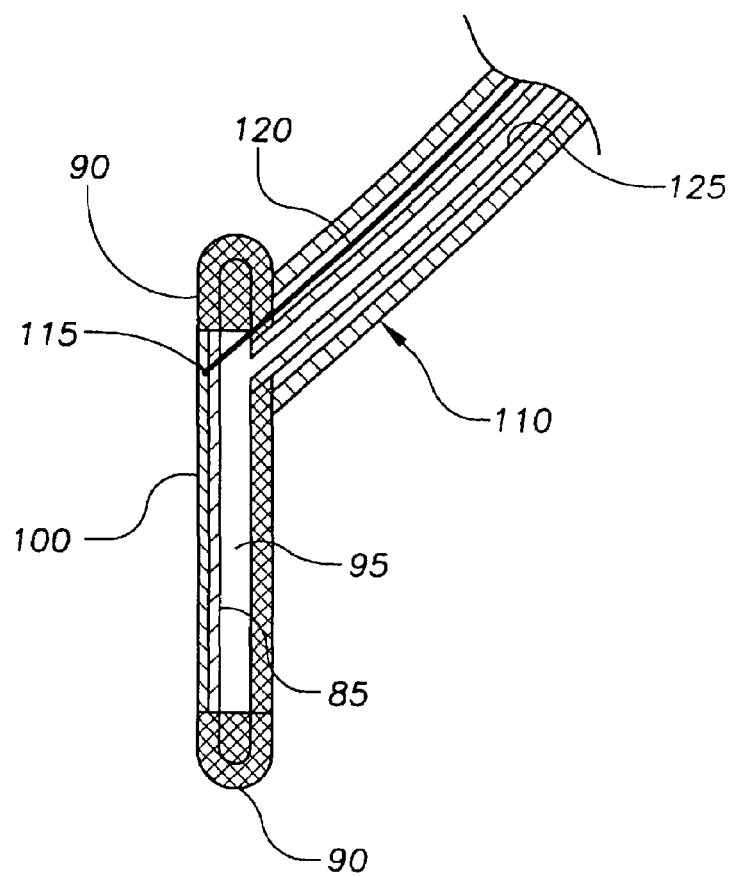

FIG. 2D is a sectional view of the patch drug delivery electrode shown in FIG. 2C that shows electrically conductive mesh 100 is connected at crimp 115 to conductor cable 120. In addition, fluid agents may travel down tube 125 within catheter body 110 to drug space 95 for uniform distribution through mesh 85.

Although shown as one large electrode used for delivering uniform energy to a large surface of tissue, many smaller electrodes could be incorporated in such a design for more precise local measurements of the heart's electrical activity, and local energy delivery. Such multi-electrode systems for epicardial placement have been described in the fields of electrical defibrillation and multi-site pacing.

The patch structures shown in FIGS. 2A, 2B, 2C, and 2D can be placed by many of the techniques described in the prior art. Many of the less invasive surgical techniques for heart access are viable such as the sub xiphoid approach. The patches may be delivered endovascularly through a transvenous approach in which the patches are delivered to the pericardial space in a collapsed form and deployed to their larger final form once within the pericardial space. The specific descriptions of transvenous access to the pericardial space here shall focus on a solution left incompletely solved in Verrier, Method for Transvenously Accessing the Pericardial Space via the Right Auricle For Medical Procedures, U.S. Pat. No. 5,269,326 (Dec. 14, 1993). The scope of this invention is not meant to be limited by this specificity, as all techniques referenced for transvenous access to the pericardium may be used. Although many techniques have been described in the prior art for crossing the atria or the vena cava to access the pericardial space, none of them solves the problem of the trans-atrial placement of an implantable device with subsequent wound closure. More importantly, none of the devices provide a means for delivering antiarrhythmic agents to the pericardial space and the surface of the heart transiently when an arrhythmic event is present.

The patches shown placed over the atria in FIG. 2a are placed with a relatively noninvasive trans-thoracic procedure in which a small incision is made between the ribs and the pericardium cut and entered with laparoscopic and microsurgical tools. The patches are placed in their appropriate places using the techniques similar to the placement of epicardial defibrillation patch leads, and the rim 105 is sutured to hold it in place, such as to either the visceral or parietal pericardium. The pericardial space is then closed, and the proximal catheters 80a and 80b are tunneled through the fascia to the region where the drug delivery pump is to be placed, typically in the subcutaneous region over the pectoral muscle. The catheters 80 are connected to the pump, and then the pump is placed within the subcutaneous pocket and the wounds are closed. Subsequent to placement, the pump reservoir can be refilled by transcutaneous injection into silicone septum 77.

Installation of local atrial drug delivery systems can be accomplished without open chest surgery, and only requires an atriotomy in the right atrial appendage. FIG. 2E shows a simple cylindrical transvenous catheter body 230 penetrating a region of atrial myocardium 200 from the endocardial side 199 to the pericardial side 201 of the myocardium. Flanges 205 and 210 are mechanically attached to catheter body 230 and shown placed on either side of the penetrated atrial wall 200. Flanges 205 and 210 are connected to one another and the interspersed atrial tissue 200 by a ring of small staples, two of which are shown as 215a and 215b. The flange structures provide reinforcement to the thin atrial tissue to provide stability for the closing staples. Catheter 230 has a distal end 220 which lies in the pericardial space and allows for infusion of the pericardium with pharmacological agents through lumen ports 225.

FIG. 2F shows an isometric view of the same catheter system shown in FIG. 2E without the presence of atrial tissue. Clearly the larger cross sectional area of the flaps 205 and 210 for securing the catheter to the atrial wall tissue make it desirable to have these structures collapsible. Although two such flaps 205 and 210 are shown in this figure, it is clear that one or even no flaps may be used in different embodiments.

FIG. 2G shows such a system with a non deployed collapsed single flap 230. Flaps could be made out of materials such as expanded polytetrafluoroethylene (ePTFE), silicone, Dacron, and combinations of these materials possible through lamination, calendering, and other techniques. In this figure the flap 230 is intended to be made out of ePTFE and be molded in its center to the catheter body at its leading edge 236. The flap 230 is pulled back and folded along fold lines 232 to its non deployed collapsed position.

Delivery of the catheter system shown in FIG. 2G can be performed with a variety of endoscopic techniques. One approach uses a monorail tip lumen on the distal end 220 of the in-dwelling catheter, such that the entire delivery catheter can be passed over a smaller guide wire type structure that has been used to penetrate the right atrial wall. In this embodiment, the catheter is implanted with a short stylet which does not protrude from the end of the catheter until the region where penetration of the atrium is desired. A sharp and short penetrating region of the stylet is then advanced from the distal end of the catheter structure, the catheter advanced through the atrial wall, and the distally protruding stylet removed. Here, the deployment of the flaps is performed by catching trailing edge 234 lip on the atrial myocardium. The catheter is inserted down through the atrial wall into the pericardial space such that the entire flap 230 advances into the pericardial space. Upon pulling back on the catheter the flap deploys in the pericardial space. Alternatively, the orientation of the flap is reversed such that the advancement of a leading edge lip causes the catheter flap 230 to deploy in the atrial endocardial space. One flap with each orientation facilitates the location of a flap on either side of the atrial myocardium. Radio opaque bands located on the catheter body at different locations also help with visualization under fluoroscopy.

A second approach for delivery of such a drug delivery catheter system could be accomplished with a larger peel away catheter. The large catheter is advanced to the region for crossing the atrial wall, and a second centrally located catheter with a sharpened tip is used to penetrate and cross the atrial wall. After the large peel away catheter has been advanced across the atrial wall, the centrally located catheter with a sharpened tip is removed, and the drug delivery catheter is advanced to the pericardial space. Here, the presence of the larger peel away catheter can be used to control the deployment of the flaps on the catheter body. In a similar technique to that described above, the flaps could be deployed by pulling the proximally located flap lip 232 against the opening of the peel away catheter for deployment. Flaps on both sides of the atrial wall are deployed in an identical fashion, and the presence of radio opaque markers would add greatly to the positioning techniques.

FIG. 2H shows a similar catheter system to that shown in FIG. 2G, except there are two deployable catheter flaps 235 and 240, both with trailing edge lips 245 and 250. In another embodiment, flap 240 would have a trailing edge lip 250 as shown, and flap 235 has a leading edge lip. Further, the proximal flap 235 may be designed to slide on the catheter 230 to facilitate the stapling process. The larger peel away guide catheter could be useful for positioning deployed flaps for subsequent surgical stapling.

FIG. 2I shows a cross section of a stapler catheter 260 advanced around the transatrial catheter 230 such that the stapler comes into contact with an endocardial flap 205 and advances it against the atrial wall 200. Such staplers would simultaneously provide a number of staples or sutures around the periphery of the catheter structure such that it repairs the atriotomy. Staples can then be delivered around the periphery of catheter body 230 to provide fixation of catheter 230 and a viable repair of the penetrated atrial wall 200. In addition, contact sensors 270, 275, 280 and 285 could be used to know that the catheter is in contact with at least the endocardial flap 205 and that flap 205 is fully deployed. By having a ring of conductive material shown in section as contact points 275 and 285 in the outside of flap 205, the stapler could monitor electrical continuity between two or more circumferentially placed electrodes 270 and 280. Continuity would imply that the flaps are deployed and that the staples may be effectively delivered.

Figure 2J:
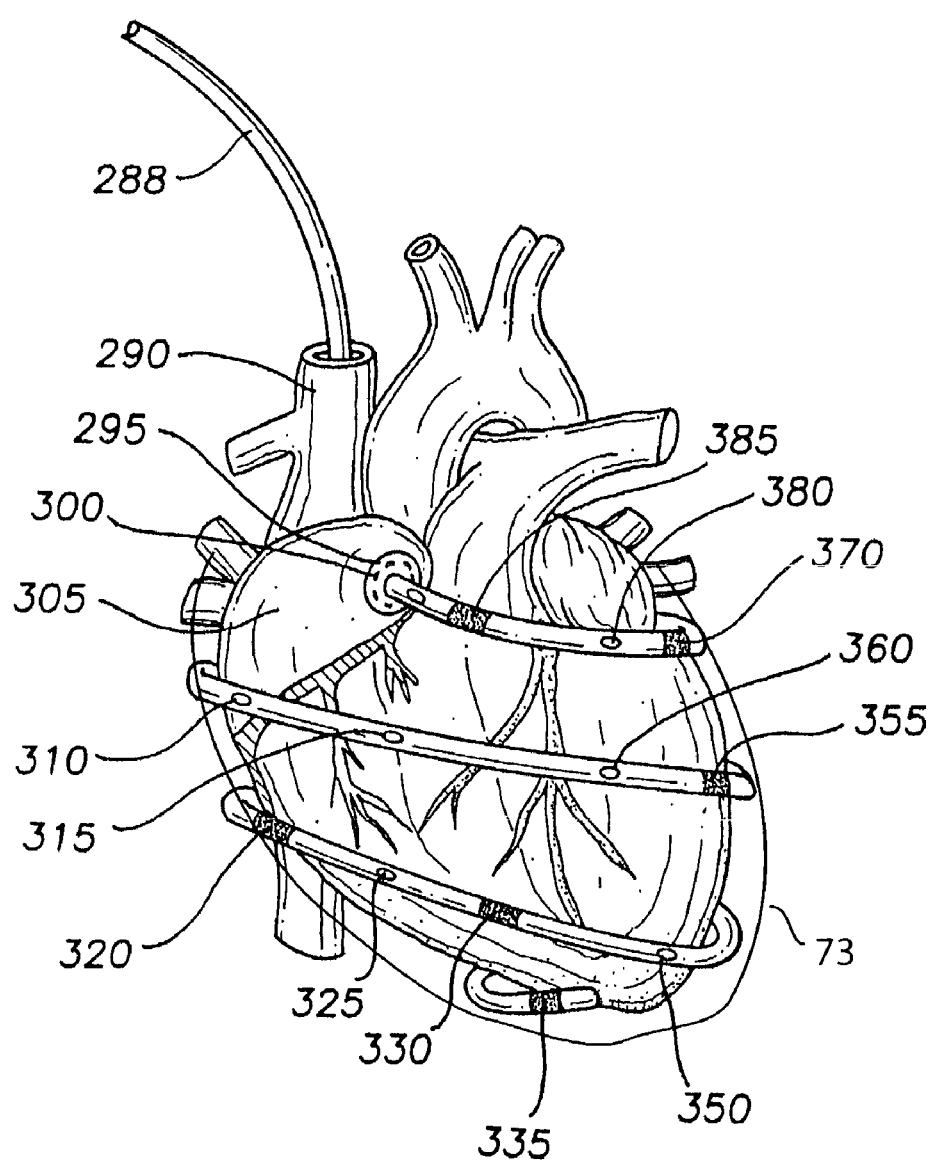
FIG. 2J illustrates a helical catheter for transatrial access to the epicardial space.

FIG. 2J shows another embodiment of the transatrial pericardial placement of a catheter for both delivery of drugs and electrical stimulation of the myocardium. Here catheter 288 enters the right atrium 305 via the superior vena cava 290 and exits the right atrium 305 via the right atrial appendage. External catheter flap 295 is shown with staples 300 securing the catheter and effecting the repair of the penetrated atrium. Cylindrical catheter 288 is advanced such that a series of electrodes can surround the heart along the catheters helical path. This view reveals a large number of electrodes 385, 370, 355, 320, 330, and 335 placed in the pericardial (or epicardial) space 73 around the heart. In addition, drug delivery ports 380, 310, 315, 360, 325, and 350 are shown such that they also surround the heart. There are many different therapies that can be achieved with such a system. This example is meant to be instructive rather than specific. For electrical stimulation, a number of electrodes could be used with an endocardial return electrode for multi-site pacing, atrial defibrillation, and ventricular defibrillation. The different electrodes could also be used for sensing activity in different regions of the heart and combined with diagnostic algorithms in implantable electrical devices (not shown). Such multielectrode catheters have an extensive history in the field of cardiac electrophysiology. The multiple drug delivery ports could be connected to different lumens within the catheter body 288, or could all be connected to a common lumen.

Figure 2K:
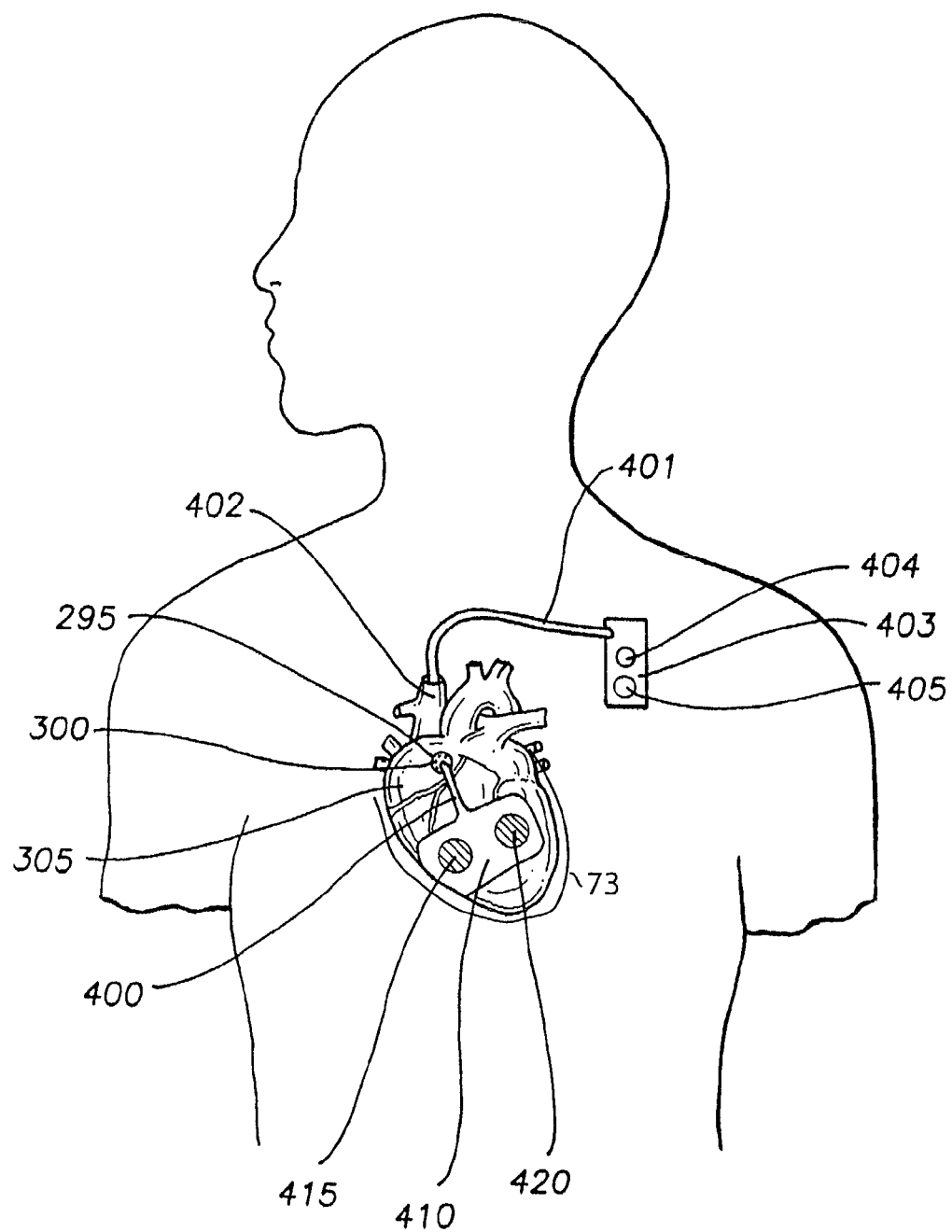
FIG. 2K illustrates an epicardial patch drug delivery system deployed from inside the right atrium.

FIG. 2K shows another embodiment of the transatrial pericardial placement of a device for both delivery of drugs and electrical stimulation of the myocardium. Here, a deployable patch system is shown placed over the ventricles in the pericardial (or epicardial) space 73. Here, larger surface area electrodes 415 and 420 are shown within a large drug delivery patch. As before, the catheter 401 enters the heart from the superior vena cava 402 and penetrates the right atrium 305. The proximal end of the catheter 401 is connected to a subcutaneously placed implantable pump and electrical stimulation device 403. Device 403 is shown with two silicone septii 404 and 405, used for filling the internal reservoir with pharmacological agents.

Figure 2L:
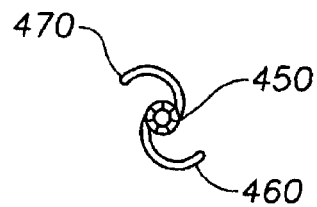
FIGS. 2L through 2O illustrate deployable epicardial patch drug delivery systems.

FIG. 2L shows one embodiment of this deployable patch structure in cross section where it is partially deployed. Arms 470 and 460 are wrapped around catheter body 450 and over one another such that they generate shadow area coverage shown in FIG. 2M when deployed. Deploying such a structure is readily done with simple mechanical techniques.

Figure 2M:
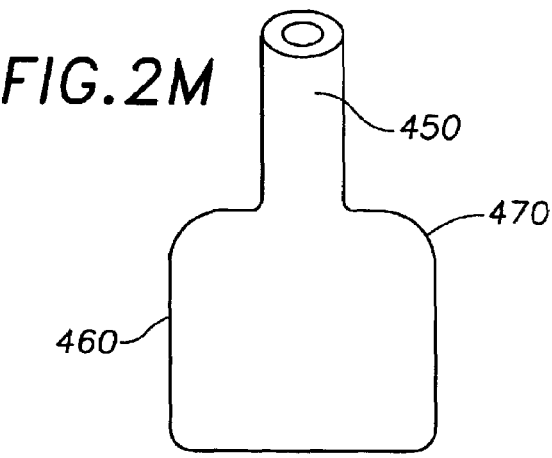
Figure 2N:
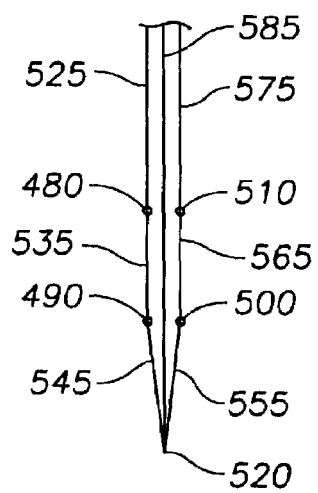
Figure 2O:
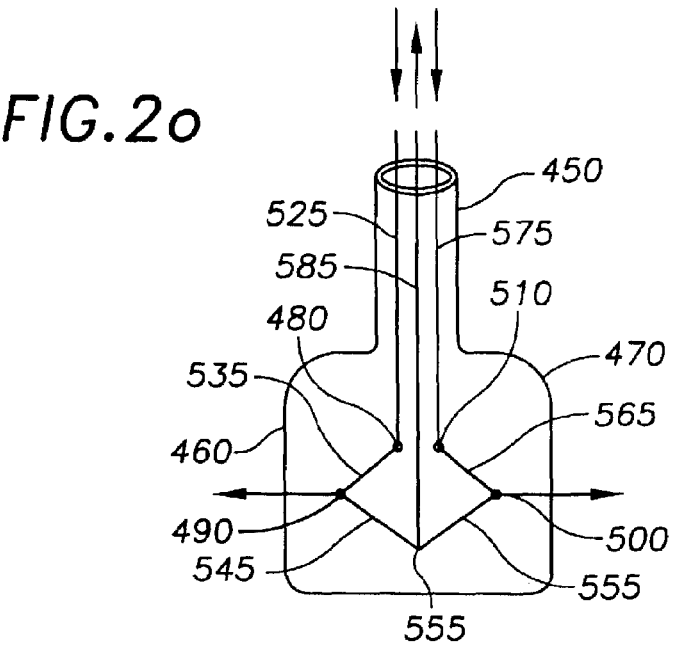

For example, FIGS. 2N and 2O show a stylet mechanism for deploying the patch shown in FIGS. 2K, 2L and 2M. Here, a simple thin wire mechanism with five hinge joints 480, 490, 500, 510, and 520 is advanced down the lumen of the patch structure to deploy the patch. FIG. 2O shows how concerted movement of stylet arms 525, 585, and 575 will result in the expansion of a planar wire structure within the deployable epicardial patch forcing it to expand. Other simple mechanisms and manipulations described in the art may also be used.

Figure 2P:
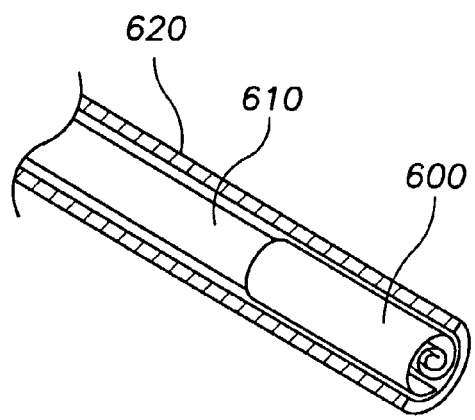
Figure 2P:
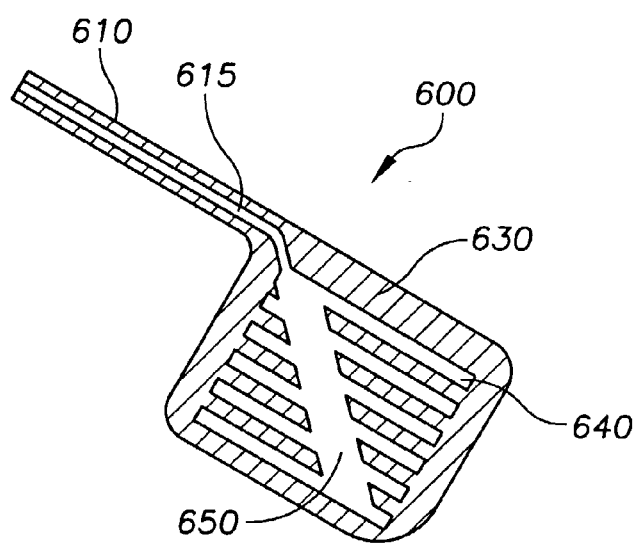
Figure 2P:
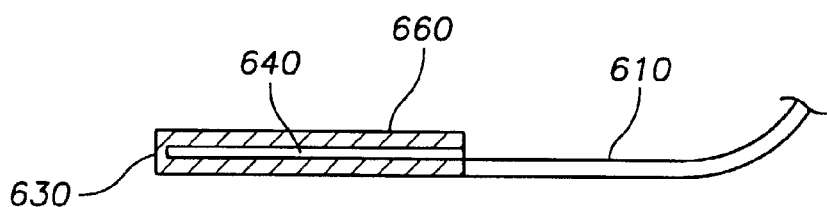

As another example, FIGS. 2P, 2Q*a*, and 2Q*b* show a rolled epicardial patch structure for distributed drug delivery to the epicardial surface. In FIG. 2P, the rolled patch structure 600 is attached to a catheter 610 that allows for the transport of drugs, and potentially the presence of electrical conductors (not shown) to connect to the rolled patch 600. The patch is advanced through the opening in the atrium by a covering tubular structure 620 from which it is advanced and deployed. This tubular delivery catheter is essentially the same as the peel away catheter system which has already been described. FIG. 2Q*a* shows a deployed patch 600 connected to catheter body 610 which is shown here to only have a lumen for drug delivery 615. It is clear to those familiar with the art that electrical conductors could be present as well. Patch 600 is shown to consist of a number of channels 640 connected by one or more transverse channels 650. Although many geometries are viable for the transverse channel, the angled pitch of the transverse channel will result in a shape that may more readily be rolled to a uniform diameter for delivery. Drug would pass down lumen 615 of body 610 and into channels 640 and 650 to be spread uniformly within the patch structure before being dispensed to the heart surface. FIG. 2Q*b* shows the same patch structure in cross section with channels 640, body 610, and molding 630. Here, a rate controlling barrier 660, such as could be formed from a microporous filter, membrane, mesh, or other structure will allow drug molecules within the transport fluid to migrate to the surface of the heart tissue. However, the resistance of the rate controlling surface 660 is greater than that through the channels 640, and the drug will be delivered relatively uniformly to the surface of the tissue to be treated.

Figure 2S:
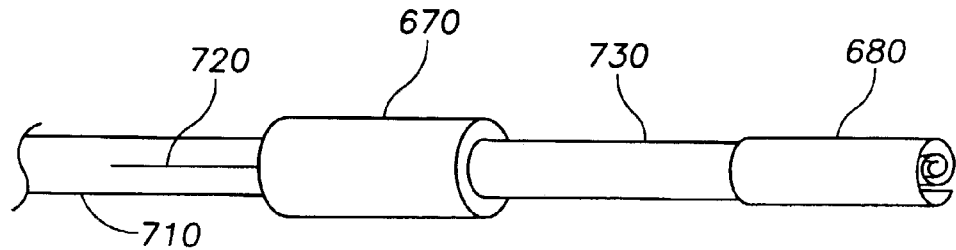
FIG. 2S is a detail view of the system of FIG. 2R.
Figure 2R:
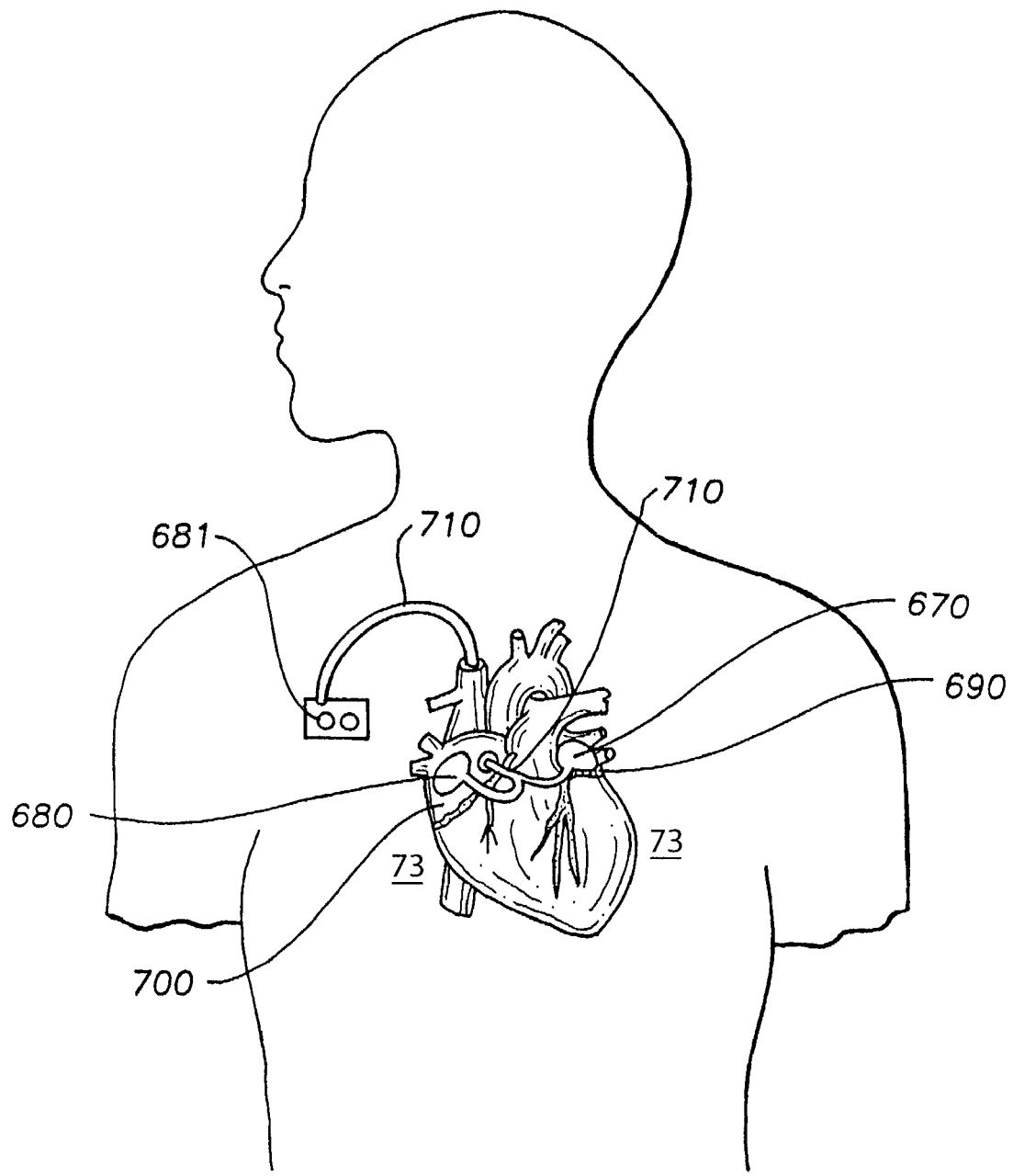
FIG. 2R illustrates an epicardial patch drug delivery system deployed from inside the right atrium.

FIG. 2R shows two similar patches 670 and 680 disposed in the pericardial (or epicardial) space 73 over the left and right atria 690 and 700. Here, these dual patches come from a single transatrial catheter body 710. This single lead body facilitates the closure and repair of the right atrial appendage or other penetrated tissue after device implantation. Here also, the implantable pump system 681 is shown implanted on the patient's right side. For crossing the atrium, different surgeons may prefer either a right or left access route. This will determine in which side of the body the device is implanted.

FIG. 2S shows one potential delivery means in which the fork 720 takes place prior to the junction of the lead body 710 and the proximal patch 670. Proximal patch 670 is wrapped around distal catheter body 730 which is connected to distal patch 680.

Delivery through a Septum of the Heart

Figure 3A:
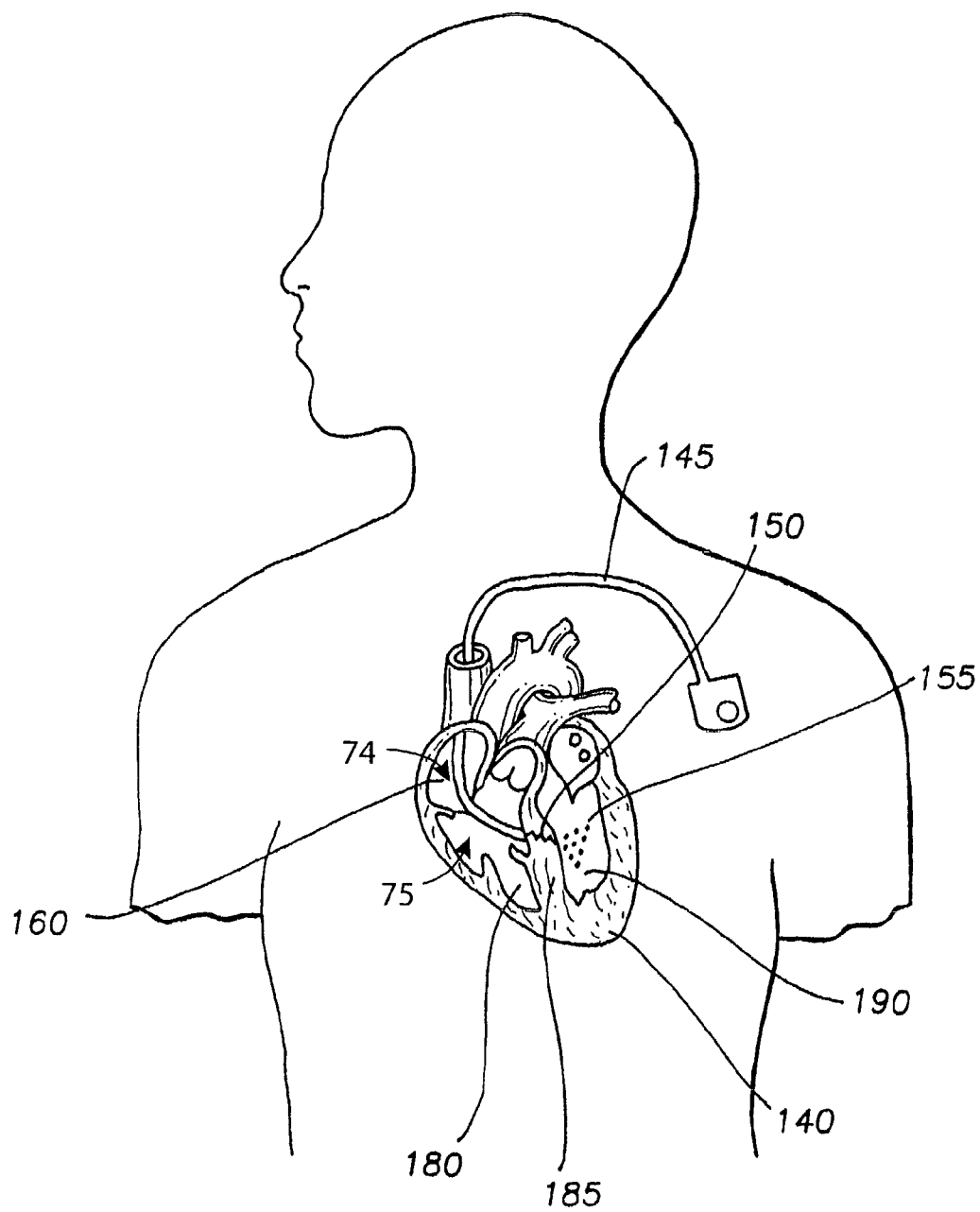
FIG. 3A is a view of an endocardial catheter installed in the right ventricle for trans-septal injection of drugs into the left ventricle.

Another embodiment for local cardiovascular drug delivery, which has particular potential for the transient termination of arrhythmias is shown in FIG. 3A. Here, a catheter system similar to that shown in FIG. 1A without the pores 20 along the length of hollow fixation structure 15, is implanted such that drug can be directly infused into the left side of the heart from a device which dwells in the right side of the heart.

FIG. 3A shows a drug delivered through the ventricular septum. Catheter 145 is inserted into the endocardial space 74 of the right atrium and the endocardial space 75 of the right ventricle 78, and is implanted in the right ventricle such that penetrating fixation device 150 is advanced through the septal wall 185. Drug delivery here occurs through the septum and into the left ventricle 190. In this way a bolus dose is delivered to the body such that it is very concentrated in its first pass through the heart.

Figure 3B:
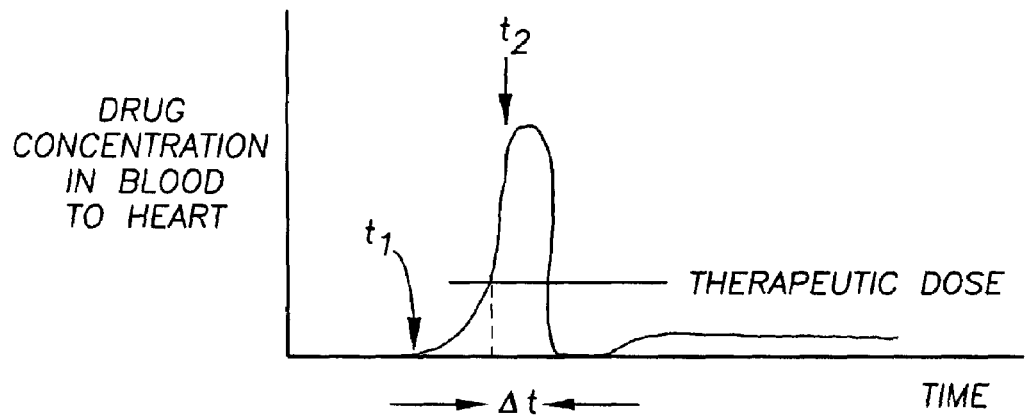
FIG. 3B illustrates the expected concentration of drugs in the heart when delivered according to the method illustrated in FIG. 3A.

This is shown reasonably well in FIG. 3B which shows a plot of the drug concentration in the heart with respect to time. Here, the drug is delivered into the left side of the heart at time t1 and enters the coronary arteries at a high concentration immediately thereafter at time t2. The duration of the dosage is very short such that by delivering a dose over a duration delta t there is only a transient therapeutic concentration within the heart. As the drug passes through the heart and begins to be further diluted with the rest of the blood, the dosage will fall below the therapeutic dose. The immediate dip after the dose is delivered is due to the lack of drug in the blood that follows the dose.

Figure 3C:
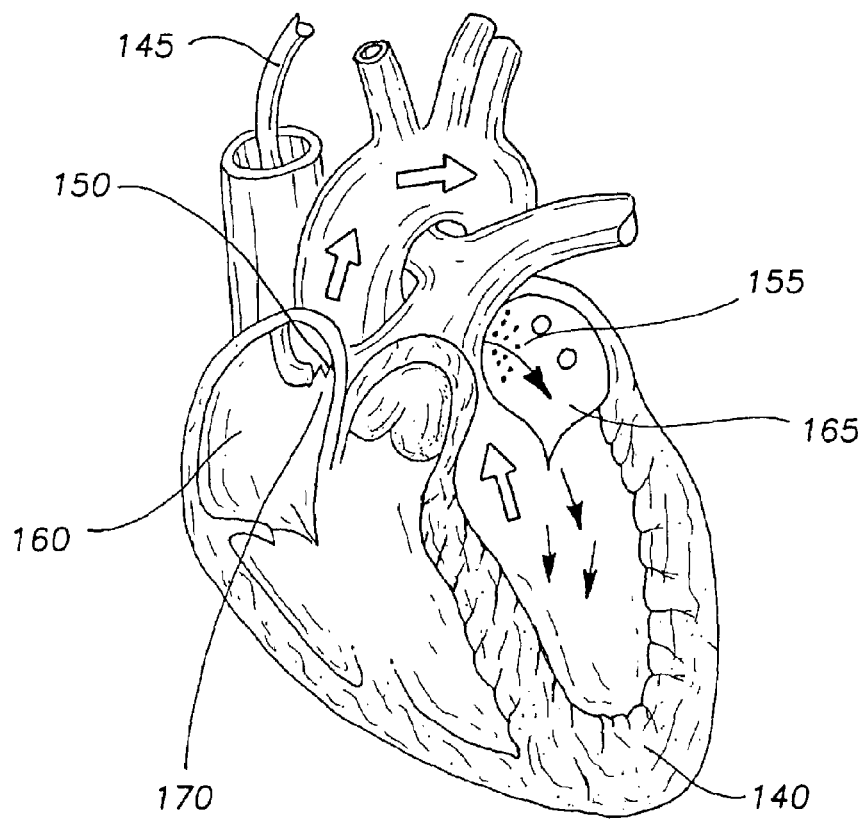
FIG. 3C shows a heart with a drug delivery catheter implanted in the right atrium.

FIG. 3C shows a heart 140 with a drug delivery catheter 145 implanted in the right atrium 160, such that the penetrating fixation device 150 is placed within the intra atrial septum 170 and the drug delivery occurs through the septum 170 and into the left atrial blood pool 155. In this way a bolus dose is delivered to the body such that it is very concentrated in its first pass through the heart. The drug in the left atrium will be diluted somewhat by the turbulent mixing as it passes in the left ventricle and it will be delivered in that concentration to the heart without dilution in the rest of the patient's effective blood volume.

The key advantage of these device methods is that they allow a means to deliver drugs to the left blood pool of the heart transiently without having a device implanted within the left side of the heart. This advantage is significant. It is very difficult to have a permanent implant in the left side of the heart because of the potentially life threatening problem of thrombus formation and stroke. In the left side of the heart small clots or thrombi could be passed to the rest of the body and obstruct critical flow to tissue such as the brain. If a device is implanted in the right side of the heart, the lungs will act as a filter to remove whatever clots and thrombi form and it is far less critical. By having a very small structure slightly penetrate the septum, drug delivery to the chambers of the left heart is achieved without the issues of a left sided implant.

Delivery Adjacent to a Heart Wall

Figure 4:
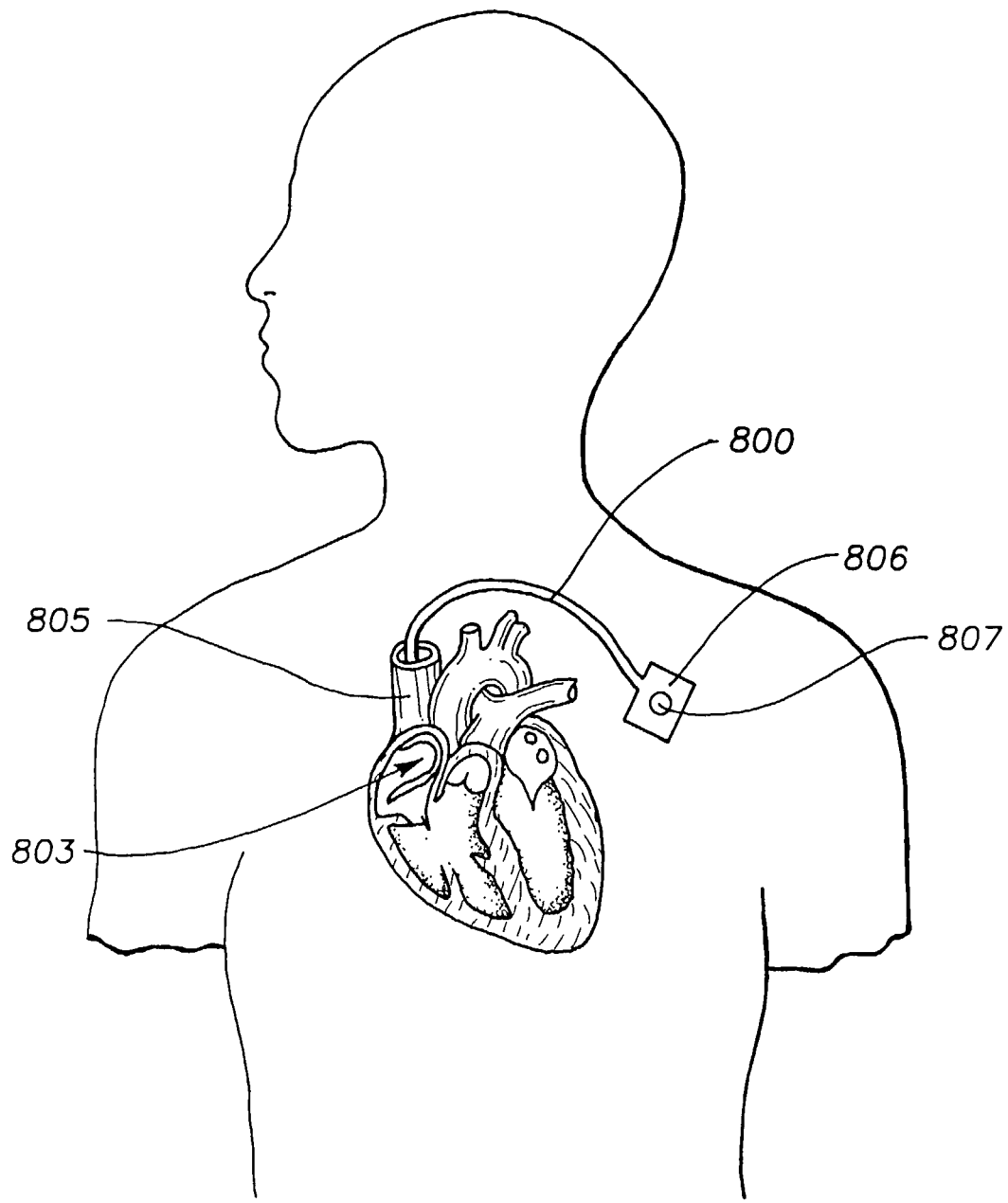
FIG. 4 illustrates a method of creating long region of block in the right atrium with a catheter.

Another embodiment for local cardiovascular drug delivery, which has particular potential for the transient termination of arrhythmias is shown in FIG. 4. Here a simple catheter is constructed so that it is extremely flexible but has a preferred curved shape 803 that will push it against the atrial wall in a preferred configuration after implantation. This can be achieved by molding a portion of the curved portion of the catheter body 803 out of polyurethane or silicone. The catheter so formed is advanced into place with a rigid stylet, such that it takes on the preferred shape after the stylet is removed. Typically in this instance a stylet is merely a long metal wire which may be shaped to provide stiffness for implantation of such catheters. Stiffness of the stylets can be varied by using different diameter wires, say from 0.010 inches to 0.020 inches and their shapes can be modified by either the physician at the time of implant or during the manufacturing process. Such stylets are well known in the field of cardiac pacing. The drug delivery catheter 800 advances into the heart from the superior vena cava 805 and is positioned by advancing and retracting different stylets until it is appropriately positioned. The proximal end of the catheter 800 is connected to a subcutaneously placed implantable pumping mechanism 806 with drug filling septum 807. The drug lumen in catheter 800 may be separate from the lumen in which the stylet is used for positioning purposes. The apertures along the distal portion of catheter 800 cannot be seen in this view because they are oriented so that they are adjacent to the heart wall.

Figure 4A:
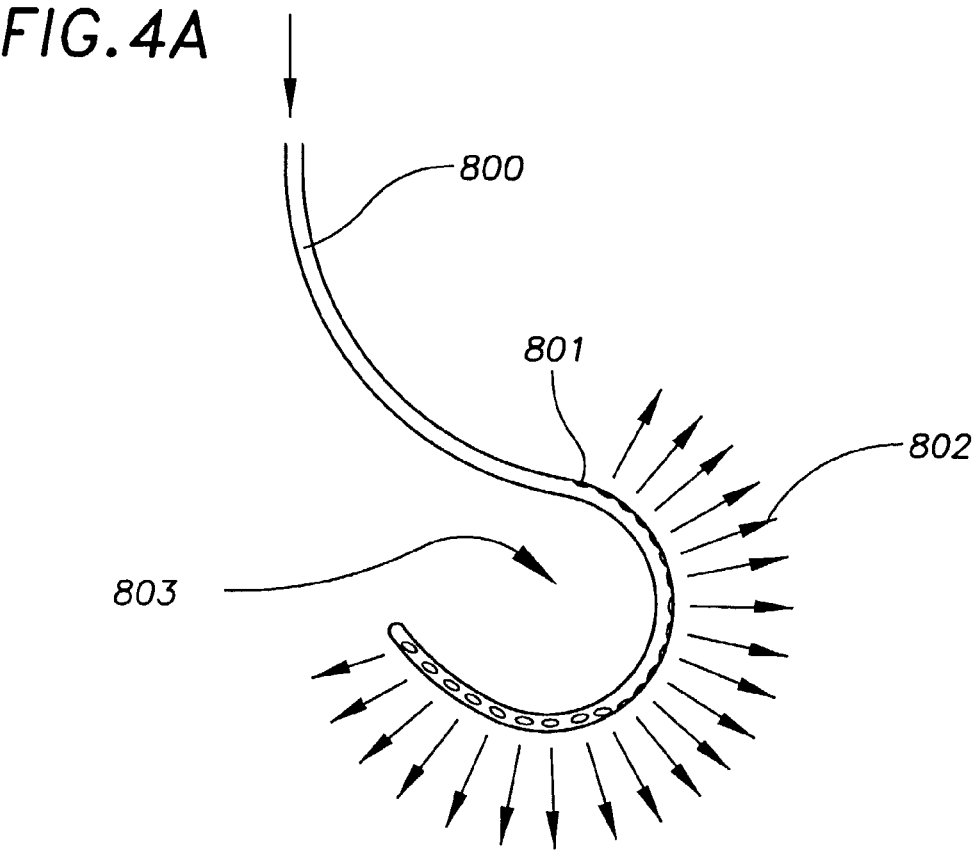
FIGS. 4A and 4B show details of the catheter of FIG. 4.

FIG. 4A shows this more clearly. Along the outer portion of the curved catheter there are a number of apertures 801 which allow fluid to be delivered preferentially towards the atrial wall 802. Such a delivery catheter would provide a means to alter a long linear region of tissue within the atrium transiently. This has great potential in treating supraventricular tachyarrhythmias.

Figure 4B:
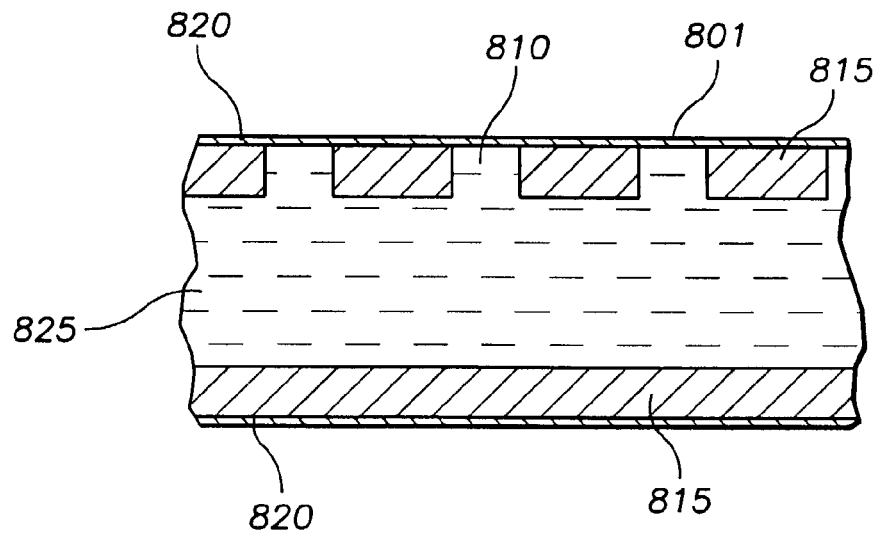

FIG. 4B shows a cross section of the catheter shown in FIG. 4A along a region of the curve 803 which includes apertures 801. Here the drug is shown in the catheter lumen 825 and passing into the holes 810 which help define the apertures 801 in the main catheter tubing body 815. It will be noted that here, catheter body 815 is covered with a thin porous structure 820 such as ePTFE which may allow adhesion of the catheter to the heart wall in the region of the apertures over time. This may be desirable as it may facilitate the delivery of agents to specific regions of the atrium to create transient linear regions of electrical slowed conduction and possibly electrical block. Roughening the surface of the catheter may be another means to promote adhesion of the catheter to the endocardial atrial surface. In other embodiments the ePTFE jacket would not be present, and the catheter would not be roughened.

Figure 5:
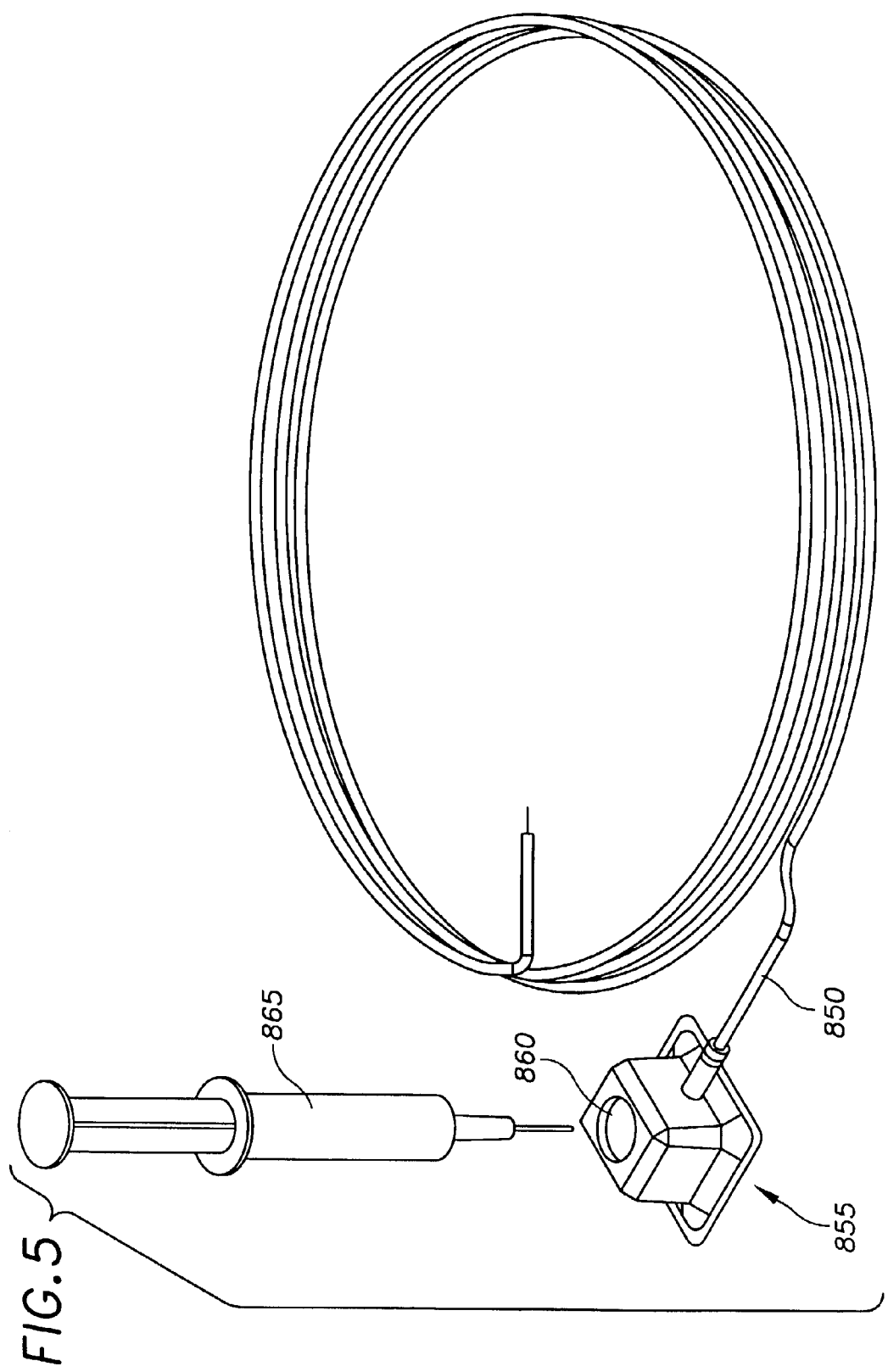
FIG. 5 illustrates the system of filling a drug reservoir to be used with the various catheters.

Part II: Methods and Devices for Transient Delivery of Agents to the Local Drug Delivery Systems Manually Triggered Drug Delivery Process In one embodiment, a permanently implantable catheter will enable the patient to deliver drugs to his or her atrium upon experiencing symptoms. FIG. 5 shows such a system. The proximal end of the catheter 850 systems described could be connected to a subcutaneous injection port 855. Such injection ports are common in the literature and often are made of a titanium body with a silicone injection septum 860. With such a device in place, a patient could self administer an injection through their skin, through the silicone septum of the device, and into the tubing which leads to the appropriate drug delivery structure embodiment. In this way, a patient recognizing an arrhythmia is able to self administer an agent to a specific location within his or her heart. By prepackaging the syringes 865, the dosages can be controlled.

An alternative approach is to provide the patient with a subcutaneous self triggered pumping device that has a reservoir filled by a physician. These are shown in FIG. 1, FIG. 2A, FIG. 2K, FIG. 2R, and FIG. 3A. Multiple therapeutic doses could be stored in such a device. Such pumping systems are already in the European market, but have not been used for this application. The self triggered pumping devices can be triggered by applying pressure to the surface of the body over the pump and depressing a diaphragm in one embodiment. In another, the pump could be an electronic device that is activated by the placement of a magnet over the device such as is known in the art of implantable electrical devices.

Instead of allowing the patient to self administer agents to themselves upon experiencing an episode, another approach is to incorporate algorithms for identifying particular arrhythmias and delivering therapy with a microprocessor based approach as described in the prior art and literature, which is hereby incorporated by reference. A microprocessor based automated pharmacological defibrillator would monitor cardiac electrical signals and deliver agents locally to the heart tissue when the electrical signals are determined by a programmed algorithm to signify that the heart is experiencing an arrhythmia.

The small doses of defibrillating pharmacological agents will be delivered to the heart tissue over a short period of time. The diffusion from the delivery sites inactivates the tissue electrically and terminates the arrhythmia. This system is relatively inexpensive to manufacture.

Part III: Hybrid Therapy

Transient cardiovascular drug delivery will improve other therapies such as implantable devices for electrical stimulation of the heart and techniques for permanent cardiac ablation.

Transient Drug Delivery and Electrical Stimulation Devices

In the first embodiment, the drug delivery systems shown in FIG. 1 and described in detail in U.S. Pat. No. 5,551,427 Altman, and in the pending application by Altman and Altman is coupled to an implantable defibrillator. Such a system is shown schematically in FIG. 6A and FIG. 6B. These systems provide the means to incorporate an algorithm that will allow the implantable system to identify a ventricular tachyarrhythmia and infuse antiarrhythmic agents into the ventricular septum in order to terminate the arrhythmia.

Typically, a tiered therapy automatic implantable cardioverter defibrillator will sense a ventricular tachyarrhythmia and identify an organized but excessive rate as ventricular tachycardia, or VT. To terminate the VT, the devices typically attempt to pace the heart at a faster rate than the tachyarrhythmia, entrain the heart at this higher rate, and then slow the paced rate below the tachyarrhythmia rate. This often does not work, and the only alternative is to deliver a painful high voltage shock to the patient to terminate the arrhythmia. Further, antitachycardia pacing has potential to accelerate the patients native arrhythmia and induce potentially life threatening ventricular fibrillation. Both of these effects of the standard therapies for VT are less than desirable. Since the reentrant circuits that drive VT are often located within the ventricular septum, it is possible with the systems shown in FIG. 6a and 6b to terminate these arrhythmias with local infusion of antiarrhythmic agents to a depth within the myocardium.

Figure 6A:
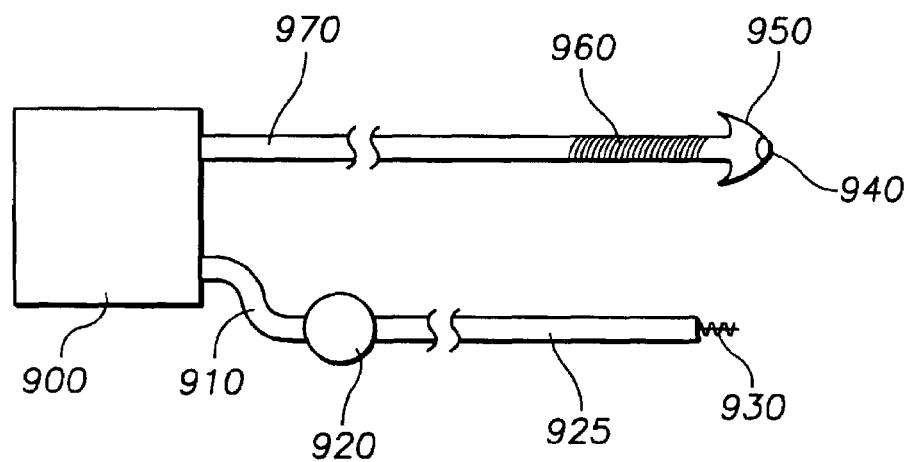
FIGS. 6A and 6B illustrate transient drug delivery catheters in combination with implantable defibrillators.

FIG. 6a shows an implantable defibrillator 900 electrically connected by lead 910 to electrically triggered pumping reservoir 920. Pumping reservoir 920 is connected to a drug delivery catheter body 925 which delivers drug to a depth within the tissue by active fixation penetrating drug delivery structure 930. Such drug delivery structures have already been described here and in the art. Defibrillator 900 is also electrically connected to implantable electrical lead 970 which has one or more defibrillation electrodes 960 along its length, and at least one pacing electrode 940 at its distal end. Implantable electrical lead also has a fixation mechanism to secure the distal end of the lead at the implantation site, which in this figure is shown to be passive tines 950. Upon detecting ventricular tachycardia, the defibrillator 900 sends an electrical signal down the lead 910 which triggers the pumping reservoir 920 to infuse the ventricular septum with antiarrhythmic agents.

It is important that the pacing/sensing electrodes 940 are physically separate from the drug delivery structure 930 for such automatic arrhythmia detection, because the infused drug will affect the ability to measure the heart's electrical action at the site of drug delivery.

Figure 6B:
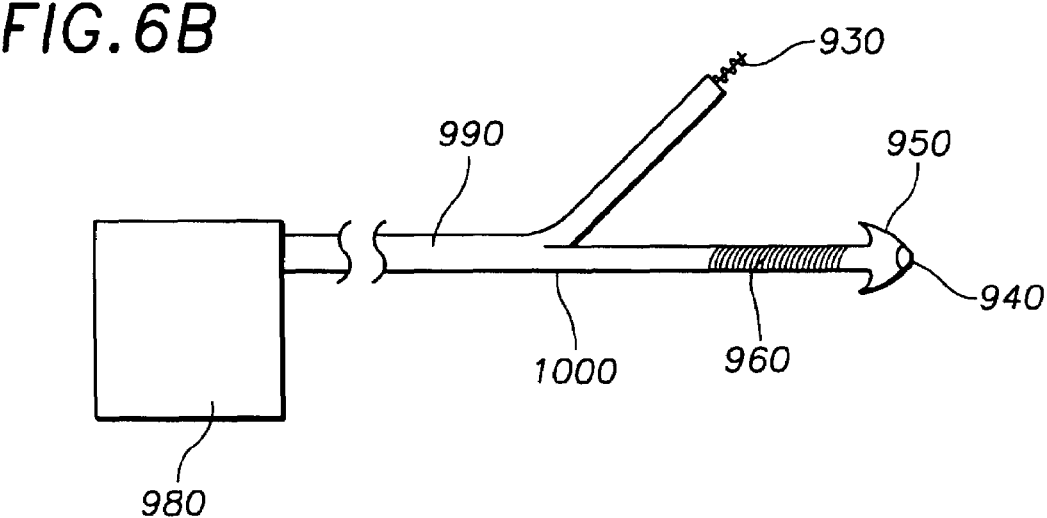

FIG. 6b shows a very similar embodiment in which the defibrillator and pump are combined in a defibrillator/pump 980 which delivers fluid and electrical energy down a single main lead body 990 which splits at 1000 to allow for spatial separation of drug delivery structure 930 and distal pacing/sensing electrodes 940.

This is just one embodiment of a means for coupling the transient delivery of electrical and local pharmacological device therapies. Drug delivery to a depth of the heart wall, to an outer surface of the heart, to the left chambers of the heart, and to long linear regions of the heart wall may be combined with electrical stimulation and sensing algorithms to provide substantially novel and unique results. Similar systems could be made combining: 1) local pharmacological atrial defibrillators with state of the art DDD pacemakers or automatic implantable cardioverter defibrillators, 2) devices to infuse drugs locally to reduce pain prior to delivering high voltage electrical energy, and 3) devices to precondition the tissue pharmacological prior to delivering electrical energy.

Transient Drug Delivery and Cardiac Ablation

In an attempt to cure atrial fibrillation, many researchers are introducing long linear lesions to the heart wall with different catheter techniques. The problem with such long lesions is that they prevent the propagation of signals through the heart even when an arrhythmia is not present, and reduce functionality of the heart. Using a drug delivery device has potential to provide flexibility in the creation of these lesions which is not currently available. An example of this is shown in FIG. 7A.

Figure 7A:
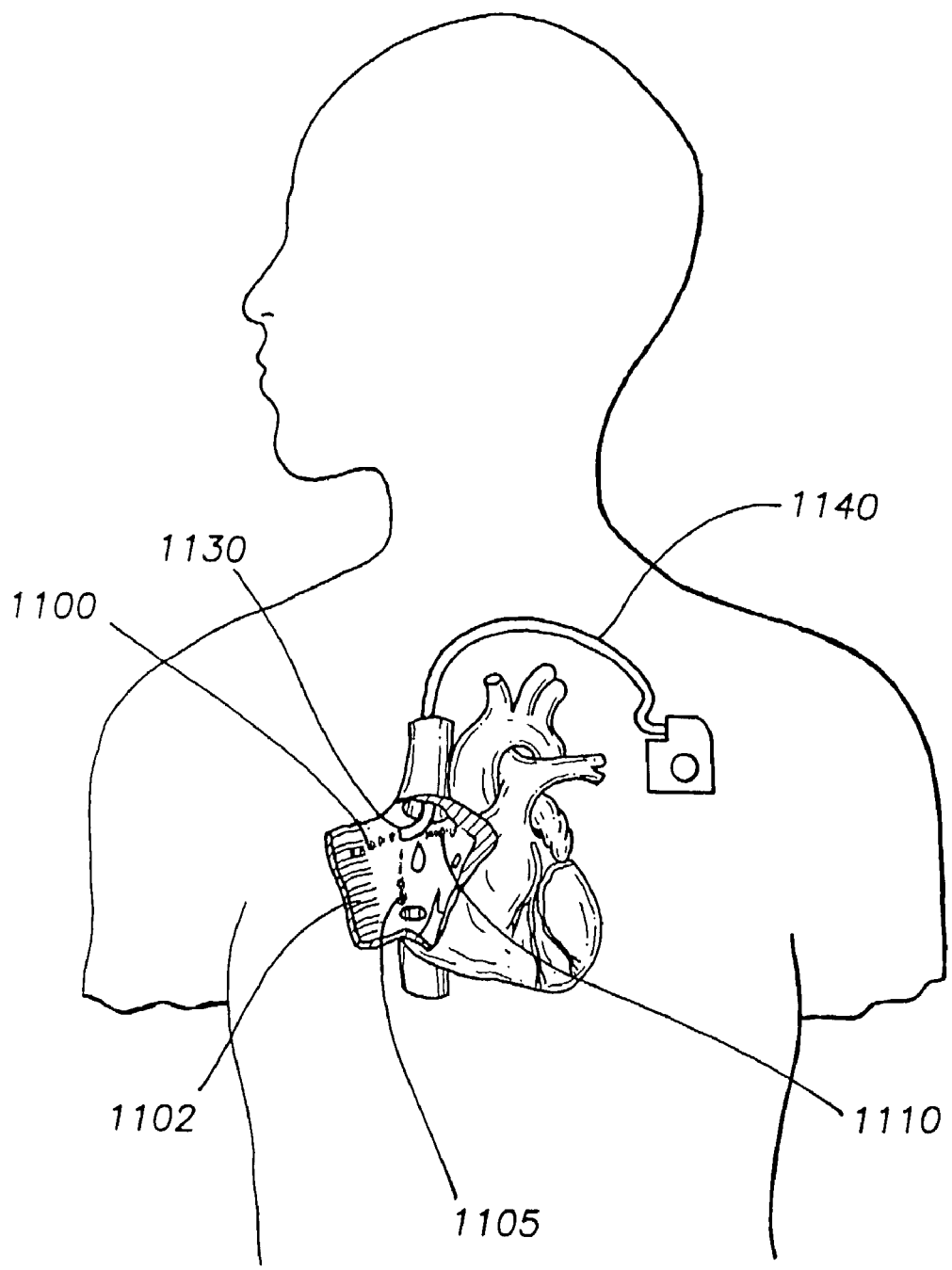
FIGS. 7A and 7B illustrate methods of transiently delivering drugs in conjunction with creating long linear lesions in the right atrium using an implanted drug delivery catheter.

FIG. 7A shows a region of atrial tissue 1102 with three long linear lesions 1100, 1105, and 1110, and placed such that electrical signals can propagate between them through the atria. In the center of these three lesions is a single penetrating drug delivery structure 1130 connected to catheter system 1140. Although the long linear lesions 1105, 1110, and 1100 are insufficient to completely eliminate the possibility of the tissue in question sustaining an arrhythmia, they are also insufficient to substantially decrease the viability of the atrial function. Upon onset of an arrhythmia, antiarrhythmic drugs (amiodorone HCl, procainimide, ibutilide, or other drugs) may be infused to a depth within the tissue by drug delivery structure 1130, and now all of the lesions 1100, 1105, and 1110 are effectively connected to one another by a region of slowed conduction. In this way, a small amount of drug delivery may be combined with lesions created by ablative techniques to complete a region of block and terminate an arrhythmia.

Figure 7B:
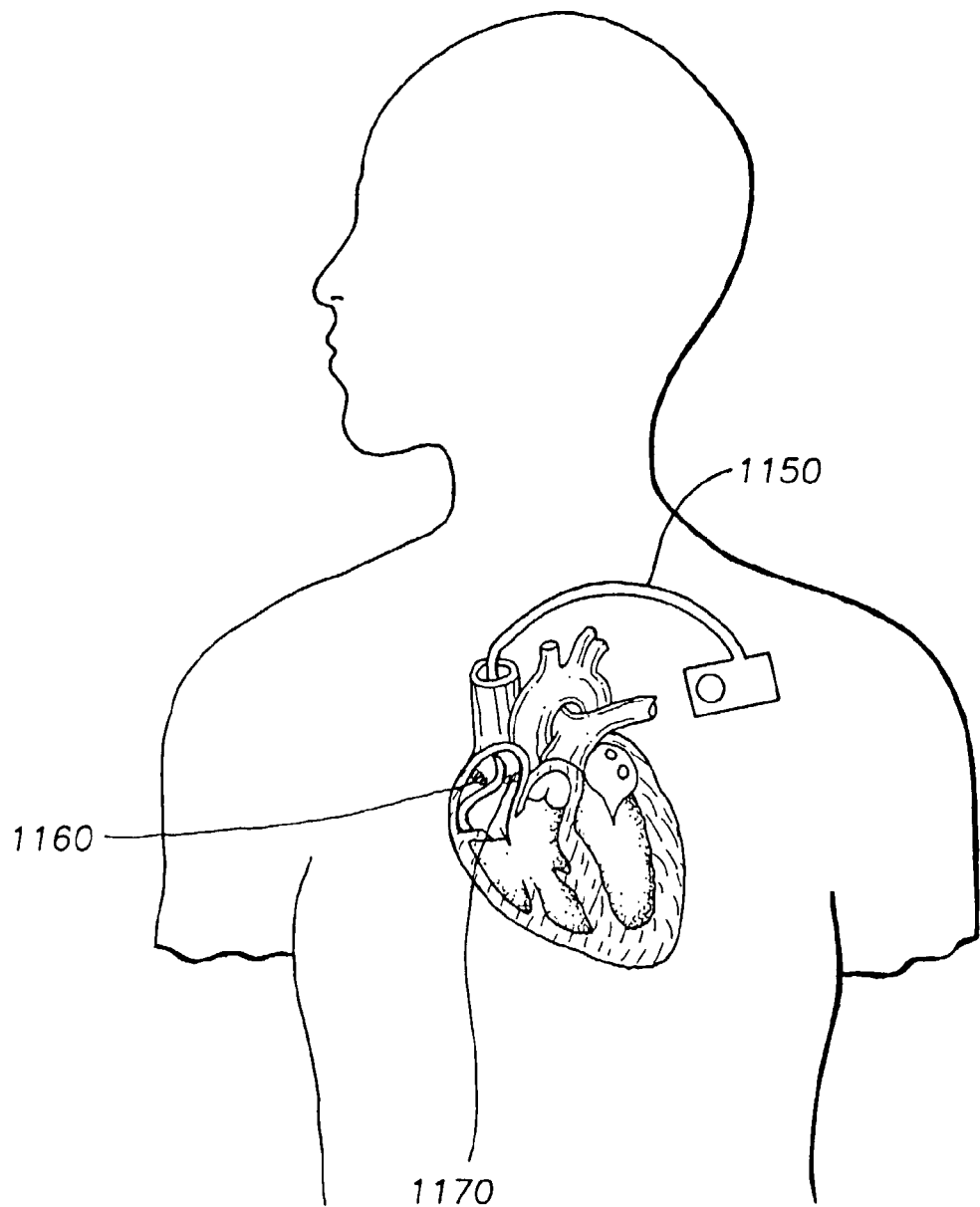

FIG. 7B shows a similar hybrid therapy approach in which the catheter 1150 similar to those shown in FIGS. 4, 4A, and 4B delivers agents to regions of the atrial wall. Here it intersects radio-frequency ablated long linear lesions 1160 and 1170 in the region where it delivers agents to the atrial wall. This connects the two linear lesions to create an impassable line of slow conducting tissue in the atrial wall. The atrium will not sustain an arrhythmia with the conductive pathways blocked by this connected and impassable line of slow conducting tissue. Clearly, other variations are also possible.

The lesions shown here are intended to be instructive, but not definitive. Many different lesion patterns are possible and techniques and approaches for creating lesions of this type are still under development.

Thus the reader will see that the different embodiments of the invention provide a means to effectively deliver agents more locally to the myocardium such that doses delivered are minimized.

They enable transient drug delivery to the tissue for treating cardiac arrhythmias, provide a means for sensing the heart, and may be combined with cardiac ablation and electrical cardiac sensing and stimulation devices.

While the above description contains many specifics, these should not be construed as limitations on the scope of the inventions, but rather as an exemplification the inventions. Many other variations are possible. For example, the flow of liquid agents may be driven by implantable infusion pumps with a variety of energy sources, and the device could be made from as yet unidentified biocompatible materials. Other examples include distally located electrically activated piezoelectric crystals or electrodes to act as energy sources for drug delivery for improving the transport into cells, distally located ultrasound transducer for implantation using ultrasound imaging. In addition, in the embodiments where bipolar sensing through the drug delivery structure is crucial, it is a simple task to add another electrode to enable bipolar sensing.

In addition, the simple penetrating designs shown in FIGS. 1, 1a, 1b, 1c, 1d, 1Ea, and 1Eb could be modified slightly to provide for a penetrating structure that protrudes through the atrial wall and into the pericardial space. By eliminating apertures along the penetrating structure such as is done in some of the earlier embodiments for delivery at a depth, therapeutic agents would only be delivered through the tissue to the pericardial space. The devices would be placed in tissue regions such as the Right atrial appendage where the tissue is thick enough to support the penetration by a small structure, and the agents would be infused through the penetrating structure to the surface of the heart. The implantation of such a device would require careful positioning such that the structure does not penetrate the aorta, but this should not be difficult.

In such a design of a small structure, such as a hollow active fixation helix, that penetrates the tissue, the successful access of the pericardial space could be determined by monitoring the pressure required to drive flow through the device. Another potential approach would be to have an electrically isolated electrode at the distal most point of the penetrating structure which could be used to pace the tissue, and the pacing threshold data used to determine whether the distal structure is in fact within the tissue, or penetrating the tissue. Such an embodiment could be useful for other embodiments all ready discussed.

Further, the delivery of the agents could be performed with appropriately modified catheter shapes such that curves are located to effect a certain position within and about the heart. Such curves in a catheter could be molded into place, or held in place by plastic deformation of the helical coil in the region it is desired. Such curved structures may provide improved access to certain regions such as the right atrium, left atrium, right ventricle and left ventricle.

Further, the drug delivery catheters could be placed using steerable guiding catheters. Acute non-implantable steerable catheters that can be secured to an implantable drug delivery catheter and steered using pull wires to place and position the different drug delivery catheters described. For acute use of the drug delivery catheters described they could be modified so that they are steerable having pull wires at the outer radii of the catheter body and potentially ribbons at the catheter midline to define the planes of bending. Many other designs are possible and have been described in the relevant art. In applications where stylets are to be used for the placement of a drug delivery catheter, it may be desirable to have an independent lumen for the delivery of fluid agents such that the stylet placement does not introduce air into the system. This can be achieved readily by having a tube which lies in parallel with the torque coil and moves in tandem with it, within the outer catheter jacket. Other potential designs include having multi-lumen tubing up until the distal end of the catheter and having a small flexible region of drug delivery tubing connected to a deployable drug delivery structure. Many other designs are possible.

For most applications, it may be appropriate to position the components relative to their implantation such that the drug delivery systems are filled with either the appropriate drug, physiological saline, or heparinized drug solution or saline at the time of implant. This would mean that the catheters would be connected to the pumping systems and sensing devices prior to implantation, and in the case of applications which require tunneling of the devices such as shown in FIG. 1, the connection would occur after a tunneling procedure which would occur before implantation of either the device or the drug delivery system. For such pre-connected systems, an external steerable guiding catheter for placement is attractive, as is an externally accessible stylet lumen that is not involved in the connection of the device to the drug delivery catheter.

Perhaps more broadening is the use for the drug delivery systems described to deliver agents for the minimization of coronary restenosis, initiation of therapeutic angiogenesis, or performing gene therapy. Such techniques would involve a more steady state approach for the delivery of therapeutic agents independent of the electrical activity of the heart. However, the systems shown here incorporate many details which are relevant for the delivery of therapeutic and diagnostic agents in general. For example, a slow steady infusion of amiodarone to a depth within the heart, or delivery of such agents on a regular basis, may prove to be advantageous and are enabled by the local drug delivery systems described here.

More than one of these systems may be implanted so that they can effect novel therapies. For example drug delivery to both the atrial and ventricular walls with separate catheters coupled to either the same or separate subcutnaeously implanted drug delivery pumps and reservoirs could be configured such that the drug delivery is controlled such that delivery to each catheter is controlled independently.

The drug delivery systems described here can be used acutely during beating heart cardiac surgery to introduce a temporary stop or marked slowing of the heart. Such induced bradycardia would provide a quiescent heart for very short periods so that delicate surgical procedures may be performed. Procedures as common and important as suturing during bypass surgery are one example of techniques that would be improved by such slowing of the heart. One example of implementation of this approach would involve a infusion of adenosine at a depth within the heart tissue adjacent to the AV node or infranodal structures with acute versions of the catheters shown in FIGS. 1A to 1F, followed after the quiescent period with temporary ventricular pacing to control haemodynamics. Additional agents could be given systemically to slow ventricular automaticity and the delivery of agents to introduce AV nodal blockade or infranodal blockade to result in a more marked slowing of the heart that could be rapidly reversed with ventricular pacing. The use of the catheter systems and local drug delivery schemes described in this disclosure are relevant for transient delivery for such slowing of the heart for improvement of surgical procedures.

Accordingly, the scope of the invention should be determined not by the embodiments illustrated, but by the appended claims and their legal equivalents.

I claim:

1. A method of treating the heart comprising:
  providing a catheter adapted for insertion into the endocardial space of the right atrium and subsequent insertion into the atrial wall and penetration of the atrial wall, said catheter comprising:
    a catheter tube with a distal section adapted for placement in the pericardial space outside the right atrium, said distal section comprising a plurality of electrodes disposed along the distal section;
    a proximal section adapted for fluid communication with a fluid reservoir located in a chest of the patient, and an intermediate section extending from the proximal section to the distal section;
    a flange disposed on the catheter at the point where the catheter penetrates the atrial wall, said flange capable of being secured to the atrial wall and forming a fluidic seal with the atrial wall;
  providing a fluid reservoir within the chest of the patient;
  inserting the distal section through the endocardial space of the right atrium, through the atrial wall so that said distal section is disposed in the epicardial space surrounding the heart;
  placing at least a portion of the intermediate section in the endocardial space of the atrium;
  securing the flange to the atrial wall;
  extending the distal section around the heart to form a helical coil surrounding the heart placing electrodes along the helical coil at multiple sites surrounding the heart;
  connecting the proximal section in fluid communication with the fluid; and
  pacing the heart at multiple sites using the plurality of electrodes.

2. The method of claim 1 wherein the catheter is further provided with a plurality of drug delivery ports along the distal section of the catheter.

3. The method of claim 1 further comprising the step of sensing activity at multiple sites in different regions of the heart along the helical coil.

4. The method of claim 2 further comprising the step of delivering drugs along the helical coil at multiple sites surrounding the heart.

* * * * *